US011633247B2

(12) United States Patent
Johnson et al.

(10) Patent No.: US 11,633,247 B2
(45) Date of Patent: Apr. 25, 2023

(54) GRAPHICAL USER GUIDANCE FOR A ROBOTIC SURGICAL SYSTEM

(71) Applicant: Verb Surgical Inc., Santa Clara, CA (US)

(72) Inventors: Eric Mark Johnson, Pacific Grove, CA (US); Michal Levin, Sunnyvale, CA (US); Anette Lia Freiin Von Kapri, Mountain View, CA (US)

(73) Assignee: Verb Surgical Inc., Santa Clara, CA (US)

( * ) Notice: Subject to any disclaimer, the term of this patent is extended or adjusted under 35 U.S.C. 154(b) by 453 days.

(21) Appl. No.: 16/807,984

(22) Filed: Mar. 3, 2020

(65) Prior Publication Data
US 2021/0275264 A1 Sep. 9, 2021

(51) Int. Cl.
*A61B 34/00* (2016.01)
*A61B 34/37* (2016.01)
*A61B 90/00* (2016.01)
*A61B 34/30* (2016.01)
(Continued)

(52) U.S. Cl.
CPC .............. *A61B 34/70* (2016.02); *A61B 34/25* (2016.02); *A61B 34/35* (2016.02); *A61B 34/37* (2016.02); *A61B 90/37* (2016.02); *G16H 40/67* (2018.01); *A61B 2034/252* (2016.02); *A61B 2034/301* (2016.02)

(58) Field of Classification Search
CPC ......... A61B 34/70; A61B 34/25; A61B 34/35; A61B 34/37; A61B 90/37; A61B 2034/252; A61B 2034/301; A61B 2017/00212; A61B 2017/00221; A61B 34/74; A61B 2034/258; A61B 34/30; G16H 40/67; G16H 20/40; G16H 30/20; G16H 40/63
See application file for complete search history.

(56) References Cited

U.S. PATENT DOCUMENTS

| 2005/0043719 A1 | 2/2005 | Sanchez et al. |
| 2007/0142825 A1 | 6/2007 | Prisco |
| 2009/0036902 A1 | 2/2009 | DiMaio et al. |
(Continued)

FOREIGN PATENT DOCUMENTS

WO   WO 2010/120407 A1   10/2010

OTHER PUBLICATIONS

International Search Report and the Written Opinion for International Patent Application PCT/US 2020/21090 dated Jun. 10, 2020.

*Primary Examiner* — Joseph M Dietrich
*Assistant Examiner* — Michael T. Holtzclaw
(74) *Attorney, Agent, or Firm* — Lempia Summerfield Katz LLC

(57) ABSTRACT

Graphical user guidance for a robotic surgical system is provided. In one embodiment, a graphical user interface for a robotic surgical system comprises a first region and a second region. The first region is used to display an endoscopic view of a surgical site inside a patient taken by an endoscopic camera of the robotic surgical system, and the second region is used to display user feedback information. The graphical user interface overlays a guidance message on top of the endoscopic view of the surgical site in the first region to provide user instructions for interacting with a user input device to engage a robotic arm of the robotic surgical system. Other embodiments are provided.

16 Claims, 19 Drawing Sheets

(51) Int. Cl.
    *G16H 40/67*     (2018.01)
    *A61B 34/35*     (2016.01)

(56) References Cited

U.S. PATENT DOCUMENTS

| | | |
|---|---|---|
| 2009/0248036 A1 | 10/2009 | Hoffman et al. |
| 2011/0125149 A1 | 5/2011 | El-galley |
| 2012/0191464 A1* | 7/2012 | Stuart .................... H04N 7/183 |
| | | 901/1 |
| 2016/0074123 A1 | 3/2016 | Bly |
| 2017/0084027 A1 | 3/2017 | Mintz |
| 2017/0143442 A1 | 5/2017 | Tesar |
| 2019/0183591 A1 | 6/2019 | Johnson et al. |
| 2019/0254759 A1* | 8/2019 | Azizian ................. A61B 90/37 |
| 2020/0093551 A1* | 3/2020 | Ishihara ................. A61B 34/74 |
| 2020/0405420 A1* | 12/2020 | Purohit ................. A61B 34/37 |
| 2021/0196399 A1* | 7/2021 | Ayvali ................... A61B 34/20 |
| 2021/0401508 A1* | 12/2021 | Zhao ..................... A61B 34/10 |

\* cited by examiner

GRAPHICAL USER GUIDANCE FOR A ROBOTIC SURGICAL SYSTEM

TECHNICAL FIELD

The following embodiments generally relate to the field of robotic surgery and more specifically to graphical user guidance for a robotic surgical system.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more surgical instruments (e.g., an end effector, at least one camera, etc.) through the incisions into the patient. The surgical procedures may then be performed using the introduced surgical instruments, with the visualization aid provided by the camera.

Generally, MIS provides multiple benefits, such as reduced patient scarring, less patient pain, shorter patient recovery periods, and lower medical treatment costs associated with patient recovery. In some embodiments, MIS may be performed with robotic systems that include one or more robotic arms for manipulating surgical instruments based on commands from an operator. A robotic arm may, for example, support at its distal end various devices, such as surgical end effectors, imaging devices, cannulae for providing access to the patient's body cavity and organs, etc.

In some embodiments, the operator may provide commands for manipulating surgical instruments while viewing an image that is provided by a camera and displayed on a display to the user.

DETAILED DESCRIPTION

Non-limiting examples of various aspects and variations of the embodiments are described herein and illustrated in the accompanying drawings.

Robotic Surgical System Overview

Figure 1A:
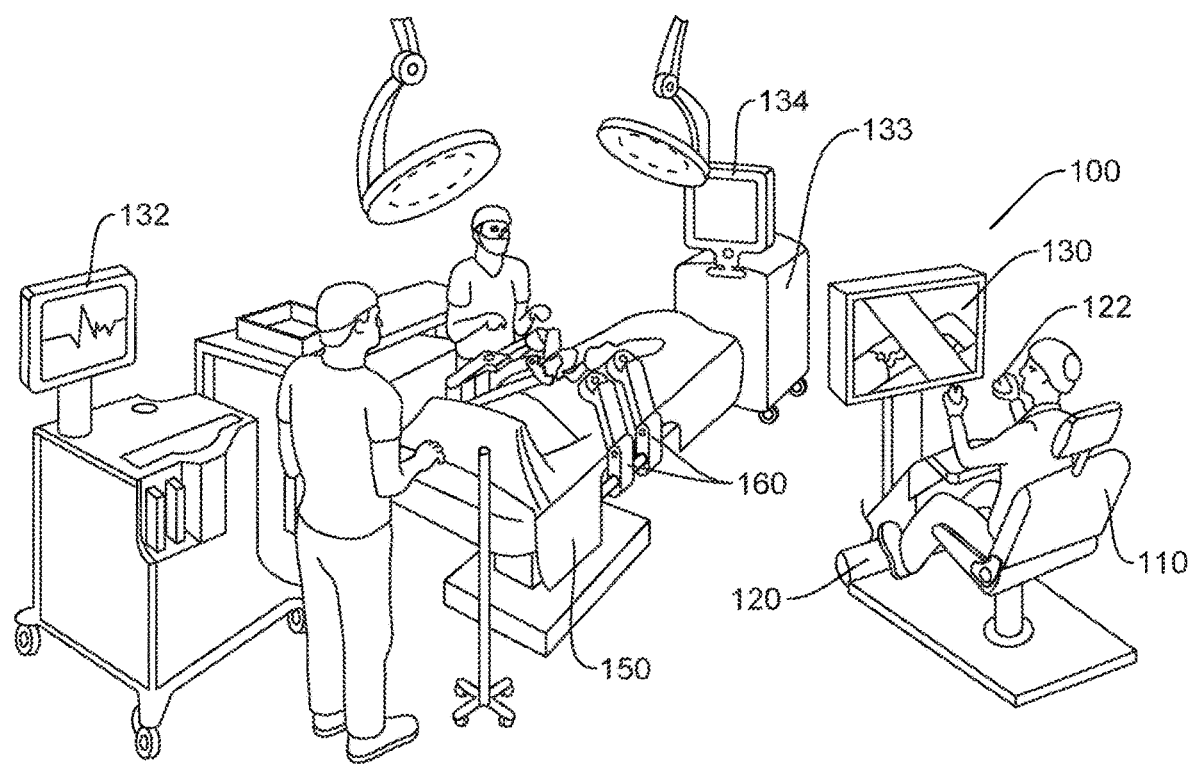
FIG. 1A depicts an example of an operating room arrangement with a robotic surgical system and a user console of an embodiment.

FIG. 1A is an illustration of an exemplary operating room environment with a robotic surgical system. Generally, as shown in FIG. 1A, the robotic surgical system includes a user console 100 (sometimes referred to herein as the "surgeon bridge" or "bridge"), a control tower 133, and one or more robotic arms 160 located at a robotic platform (e.g., table, bed, etc.), where surgical instruments (e.g., with end effectors) are attached to the distal ends of the robotic arms 160 for executing a surgical procedure. The robotic arms 160 are shown as a table-mounted system, but in other configurations, one or more robotic arms may be mounted to a cart, ceiling or sidewall, or other suitable support surface.

Figure 1B:
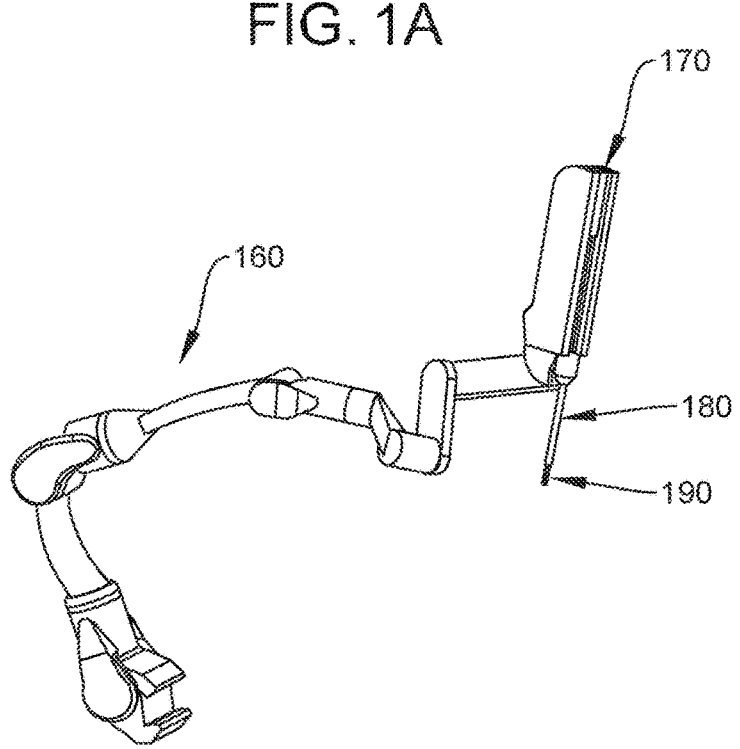
FIG. 1B is a schematic illustration of one exemplary variation of a robotic arm manipulator, tool driver, and cannula with a surgical tool of an embodiment.

As further illustration, as shown in the exemplary schematic of FIG. 1B, a robotic surgical system may include at least one robotic arm 160 and a tool driver 170 generally attached to a distal end of the robotic arm 160. A cannula 180 coupled to the end of the tool driver 170 may receive and guide a surgical instrument 190 (e.g., end effector, camera, etc.). Furthermore, the robotic arm 160 may include a plurality of links that are actuated so as to position and orient the tool driver 170, which actuates the surgical instrument 190.

Generally, as shown in FIG. 1A, the user console 100 may be used to interface with the robotic surgical system 150. A user (such as a surgeon or other operator) may use the user console 100 to remotely manipulate the robotic arms 160 and/or surgical instruments (e.g., in tele-operation). The user console 100 may be located in the same operating room as the robotic system 150, as shown in FIG. 1A. In other embodiments, the user console 100 may be located in an adjacent or nearby room, or tele-operated from a remote location in a different building, city, or country. In one example, the user console 100 may comprise a seat 110, foot-operated controls (pedals) 120, one or more handheld user input devices 122, and at least one user display 130 configured to display, for example, a view of the surgical site inside a patient (e.g., captured with an endoscopic camera), and/or other surgical or medical information.

Figure 1C:
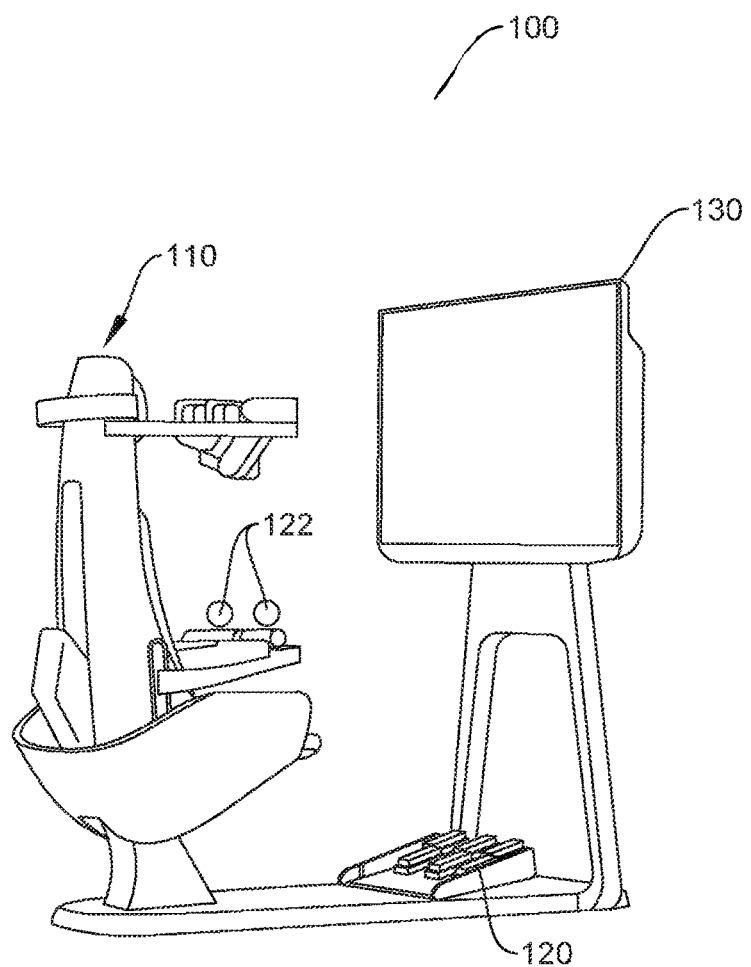
FIG. 1C is a schematic illustration of an exemplary user console of an embodiment.

In the exemplary user console shown in FIG. 1C, a user located in the seat 110 and viewing the user display 130 may manipulate the foot-operated controls 120 and/or handheld user input devices 122 to remotely control the robotic arms 160 and/or surgical instruments mounted to the distal ends of the arm. The foot-operated controls 120 and/or handheld user input devices 122 may additionally or alternatively be used to control other aspects of the user console 100 or robotic system 150. For example, in variations in which the user generally controls (at any given time) a designated "left-hand" robotic arm/instrument and a designated "right-hand" robotic arm/instrument, the foot-operated controls 120 may enable a user to designate from among a larger group of available robotic arms/instruments which robotic arms/instruments comprise the "left-hand" and "right-hand" robotic arm/instruments (e.g., via toggle or rotation in selection among the available robotic arms/instruments). Other examples include adjusting or configuring the seat 110, the foot-operated controls 120, the user input devices 122, and/or the user display 130.

In some variations, a user may operate the surgical robotic system in an "over the bed" (OTB) mode, in which the user is at the patient's side and simultaneously manipulating a robotically-driven instrument/end effector attached thereto (e.g., with a handheld user input device 122 held in one hand) and a manual laparoscopic tool. For example, the user's left hand may be manipulating a handheld user input device 122 to control a robotic surgical component, while the user's right hand may be manipulating a manual laparoscopic tool. Accordingly, in these variations, the user may perform both robotic-assisted MIS and manual laparoscopic surgery on a patient.

During an exemplary procedure or surgery, the patient is prepped and draped in a sterile fashion, and anesthesia may be achieved. Initial access to the surgical site may be performed manually with the robotic system 150 in a stowed configuration or withdrawn configuration to facilitate access to the surgical site. Once access is completed, initial positioning and/or preparation of the robotic system may be performed. During the surgical procedure, a surgeon or other user in the user console 100 may utilize the foot-operated controls 120, user input devices 122, and/or other suitable controls to manipulate various end effectors and/or imaging systems to perform the procedure. Manual assistance may be provided at the procedure table by other personnel, who may perform tasks including but not limited to retracting tissues, or performing manual repositioning or tool exchange involving one or more robotic arms 160. Other personnel may be present to assist the user at the user console 100. Medical and surgery-related information to aid other medical personnel (e.g., nurses) may be provided on additional displays such as a display 134 on a control tower 133 (e.g., control system for the robotic surgical system) and/or a display 132 located bedside proximate the patient. For example, as described in further detail herein, some or all information displayed to the user in the user console 100 may also be displayed on at least one additional display for other personnel and/or provide additional pathways for inter-personnel communication. When the procedure or surgery is completed, the robotic system 150 and/or user console 100 may be configured or set in a state to facilitate one or more post-operative procedures, including but not limited to robotic system cleaning and/or sterilization, and/or healthcare record entry or printout, whether electronic or hard copy, such as via the user console 100.

In some variations, the communication between the robotic system 150, the user console 100, and any other displays may be through the control tower 133, which may translate user commands from the user console 100 to robotic control commands and transmit them to the robotic system 150. The control tower 133 may transmit status and feedback from the robotic system 150 back to the user console 100 (and/or other displays). The connections between the robotic system 150, the user console 100, other displays, and the control tower 133 may be via wired and/or wireless connections, and may be proprietary or performed using any of a variety of data communication protocols. Any wired connections may be built into the floor and/or walls or ceiling of the operating room. The robotic surgical system may provide video output to one or more displays, including displays within the operating room as well as remote displays accessible via the Internet or other networks. The video output or feed may be encrypted to ensure privacy, and all or one or more portions of the video output may be saved to a server, an electronic healthcare record system, or other suitable storage medium.

In some variations, additional user consoles 100 may be provided, for example to control additional surgical instruments, and/or to take control of one or more surgical instruments at a primary user console. This will permit, for example, a surgeon to take over or illustrate a technique during a surgical procedure with medical students and physicians-in-training, or to assist during complex surgeries requiring multiple surgeons acting simultaneously or in a coordinated manner.

Figure 2:
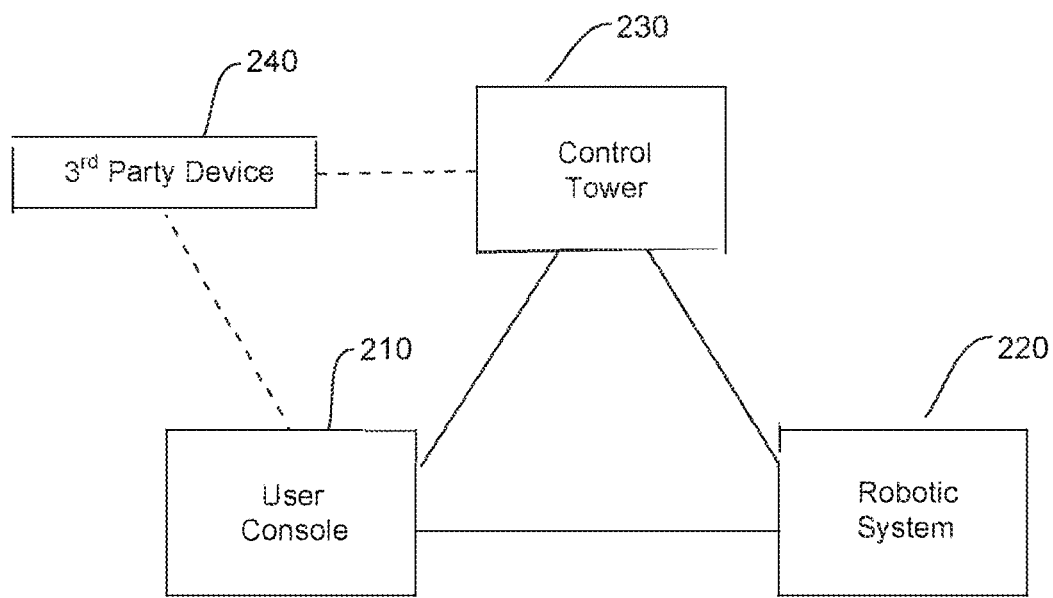
FIG. 2 is a schematic illustration of an exemplary variation of a user console for a robotic surgical system of an embodiment in communication with one or more third party devices.

In some variations, as shown in the schematic illustration of FIG. 2, one or more third party devices 240 may be configured to communicate with the user console 210 and/or other suitable portions of the robotic surgical system. For example, as described elsewhere herein, a surgeon or other user may sit in the user console 210, which may communicate with the control tower 230 and/or robotic instruments in a robotic system 220. Medical data (e.g., endoscopic images, patient vitals, tool status, etc.) may be displayed at the user console 210, the control tower 230, and/or other displays. At least a subset of the surgical and other medical-related information may furthermore be displayed at a third party device 240, such as a remote computer display that is viewed by a surgical collaborator in the same room or outside the room. Other communication, such as teleconferencing with audio and/or visual communication, may further be provided to and from the third party device. The surgical collaborator may be, for example, a supervisor or trainer, a medical colleague (e.g., radiologist), or other third party who may, for example, view and communicate via the third party device 240 to assist with the surgical procedure.

Figure 3:
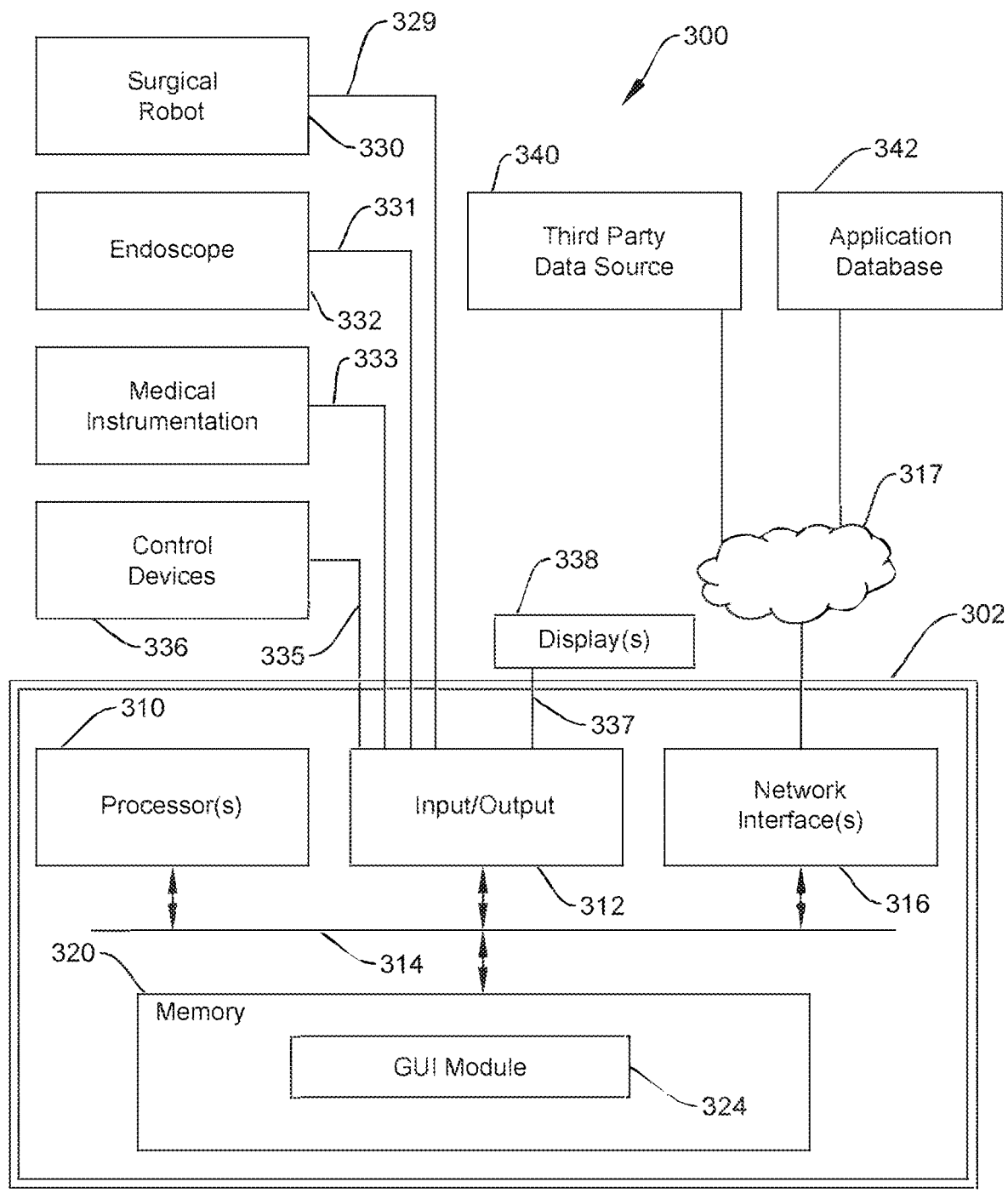
FIG. 3 is a schematic of a surgical robotic platform of an embodiment with a graphical user interface (GUI) module, where the surgical robotic platform is in communication with multiple medical data resources.

FIG. 3 is a schematic illustration of an exemplary variation of a system 300 including a robotic surgical system and its interaction with other devices and parties. Although a particular architecture of the various connected and communicating systems is depicted in FIG. 3, it should be understood that in other variations, other suitable architectures may be used and the arrangement shown in FIG. 3 is for illustrative purposes. The system 300 may include a surgical robotic platform 302 that facilitates the integration of medical data from discrete medical data resources generated from a variety of parties. Data from the discrete medical data resources may, for example, be used to form temporally coordinated medical data. Multi-panel displays of the temporally coordinated medical data may be configured and presented, as described further herein.

The platform 302 may be, for example, a machine with one or more processors 310 connected to one or more input/output devices 312 via a bus 314. The at least one processor may, for example, include a central processing unit, a graphics processing unit, an application specific integrated circuit, a field programmable logic device or combinations thereof.

The surgical robotic platform 302 may include one or more input ports to receive medical data from discrete medical data resources. For example, a surgical robot port 329 may receive surgical robot data from a surgical robot 330. Such data may, for example, include position data or other suitable status information. An imaging port 331 may receive imaging data from an imaging device 332, such as an endoscope, that is configured to capture images (e.g., still images, video images) of a surgical site. The endoscope may, for example, be inserted through a natural orifice or through an aperture in a surgical patient. As another example, one or more medical instrumentation ports 333 may receive patient vital information from medical instrumentation 334 (e.g., a pulse oximeter, electrocardiogram device, ultrasound device and/or the like). Additionally, as another example, one or more user control data ports 335 may receive user interaction data from one or more control devices that receive user inputs from a user for controlling the system. For example, one or more handheld user input devices, one or more foot pedals, and/or other suitable devices (e.g., eye tracking, head tracking sensors) may receive user inputs.

The surgical robotic platform 302 may further include one or more output ports 337 configured for connection to one or more displays 338. For example, the displays 338 may include an open display (e.g., monitor screen) in a user console, an immersive display or head-mounted device with a display, on supplemental displays such as on a control tower display (e.g., team display), a bedside display (e.g., nurse display), an overhead "stadium"-style screen, etc. For example, the graphical user interface disclosed herein may be presented on one or more displays 338. The one or more displays 338 may present three-dimensional images. In some variations, the one or more displays 338 may include a touchscreen. The one or more displays 138 may be a single display with multiple panels, with each panel presenting different content. Alternatively, the one or more displays 138 may include a collection of individual displays, where each individual display presents at least one panel.

In some variations, a network interface 316 may also be connected to the bus 314. The network interface 316 may, for example, provide connectivity to a network 317, which may be any combination of one or more wired and/or wireless networks. The network 317 may, for example, help enable communication between the surgical robotic platform 302 and other data sources or other devices. For example, one or more third party data sources 340 may also be connected to the network 317. The third party source 340 may include a third party device (e.g., another computer operated by a third party such as another doctor or medical specialist), a repository of video surgical procedure data (e.g., which may be relevant to a procedure being performed by a surgeon), or other suitable source of additional information related to a surgical procedure. For example, the third party device data may be ported to a panel that is displayed to a surgeon before, during or after a procedure.

As another example, one or more application databases 342 may be connected to the network 317 (or alternatively, stored locally within a memory 320 within the surgical robotic platform 302). The application database 342 may include software applications (e.g., as described in further detail below) that may be of interest to a surgeon during a procedure. For example, a software application may provide access to stored medical records of a patient, provide a checklist of surgical tasks for a surgical procedure, perform machine vision techniques for assisting with a procedure, perform machine learning tasks to improve surgical tasks, etc. Any suitable number of applications may be invoked. Information associated with an application may be displayed in a multi-panel display or other suitable display during a procedure. Additionally or alternatively, information provided by one or more applications may be provided by separate resources (e.g., a machine learning resource) otherwise suitably in communication with the surgical robotic platform 302.

In some variations, one or more of the software applications may run as a separate process that uses an application program interface (API) to draw objects and/or images on the display. APIs of different complexities may be used. For example, a simple API may include a few templates with fixed widget sizes and locations, which can be used by the GUI module to customize text and/or images. As another example, a more complex API may allow a software application to create, place, and delete different widgets, such as labels, lists, buttons, and images.

Additionally or alternatively, one or more software applications may render themselves for display. This may, for example, allow for a high level of customization and complex behavior for an application. For example, this approach may be implemented by allowing an application to pass frames that are rendered by a graphical user interface (GUI) module 324, which can be computer-readable program code that is executed by the processor 310. Alternatively, an image buffer may be used as a repository to which an application renders itself.

In some variations, one or more software applications may run and render themselves independent of the GUI module 324. The GUI module may still, however, launch such applications, instruct the application or the operating system where the application is to be positioned on the display, etc.

As another approach, in some variations, one or more applications may run completely separate from the GUI rendered by the GUI module. For example, such applications may have a physical video connection and data connection to the system (e.g., through suitable input/output devices, network, etc.). The data connection may be used to configure video feed for an application to be the appropriate pixel dimensions (e.g., full screen, half screen, etc.).

As shown in FIG. 3, in some variations, a memory 320 may also be connected to the bus 314. The memory 320 may be configured to store data processed in accordance with embodiments of the methods and systems described herein.

In some variations, the memory 320 may be configured to store other kinds of data and/or software modules for execution. For example, a user console may include a memory 320 that stores a GUI module 324 with executable instructions to implement operations disclosed herein. The GUI module may, for example, combine and aggregate information from various software applications and/or other medical data resources for display. In some exemplary variations, one or more software applications may be incorporated into base code of the GUI module, such that the module draws graphics and displays text in the appropriate location on the display. For example, the module may fetch the images from a database, or the images may be pushed to the interface from an instrument (e.g., endoscopic camera) in the operating room, via a wired or wireless interface.

In some variations, medical data may be collected from discrete medical data resources (e.g., surgical robot 330, endoscope 332, medical instrumentation 334, control devices 336, third party data source 340, application database 342, etc.). Additionally, at least some of the medical data may be temporally coordinated such that, when necessary, time sensitive information from different medical data resources is aligned on a common time axis. For example, surgical robot position data may be time coordinated with endoscope data, which is coordinated with operator interaction data from control devices. Similarly, a networked resource, such as information provided by one or more software applications, may be presented at an appropriate point in time along with the other temporally coordinated data. Multi-panel displays, and/or other suitable displays, may be configured to communicate medical information (e.g., including the temporally coordinated medical data) as part of a graphical user interface (GUI).

Various exemplary aspects of a GUI for a robotic surgical system are described herein. In some variations, the GUI may be displayed in a multi-panel display at a user console that controls the robotic surgical system. Additionally or alternatively, the GUI may be displayed at one or more additional displays, such as at a control tower for the robotic surgical system, at a patient bedside, etc. Generally, the GUI may provide for more effective communication of information to a user in the user console and/or other personnel, as well as for more effective communication and collaboration among different parties involved in a surgical procedure, as further described below.

Graphical User Interface (GUI) Interaction

In one embodiment, the GUI is displayed on a display 130 in a user console 100 that is used to control the robotic surgical system 150 (e.g., by a surgeon), and at least some of interactive graphical objects displayed on the display 130 may be controlled, selected, or otherwise interacted with via one or more user controls that are also used to control an aspect of the surgical system (e.g., surgical instrument). For example, a user may use one or more handheld user input devices 122 and/or one or more foot pedals 120 to selectively control an aspect of the robotic surgical system 150 and selectively interact with the GUI. By enabling control of both the robotic surgical system 150 and the GUI with the same user controls, the user may advantageously avoid having to switch between two different kinds of user controls. Enabling the user to use the same input devices to control the robotic system 150 and the GUI streamlines the surgical procedure and increases efficiency, as well as helps the user maintain sterility throughout a surgical procedure.

Figure 4A:
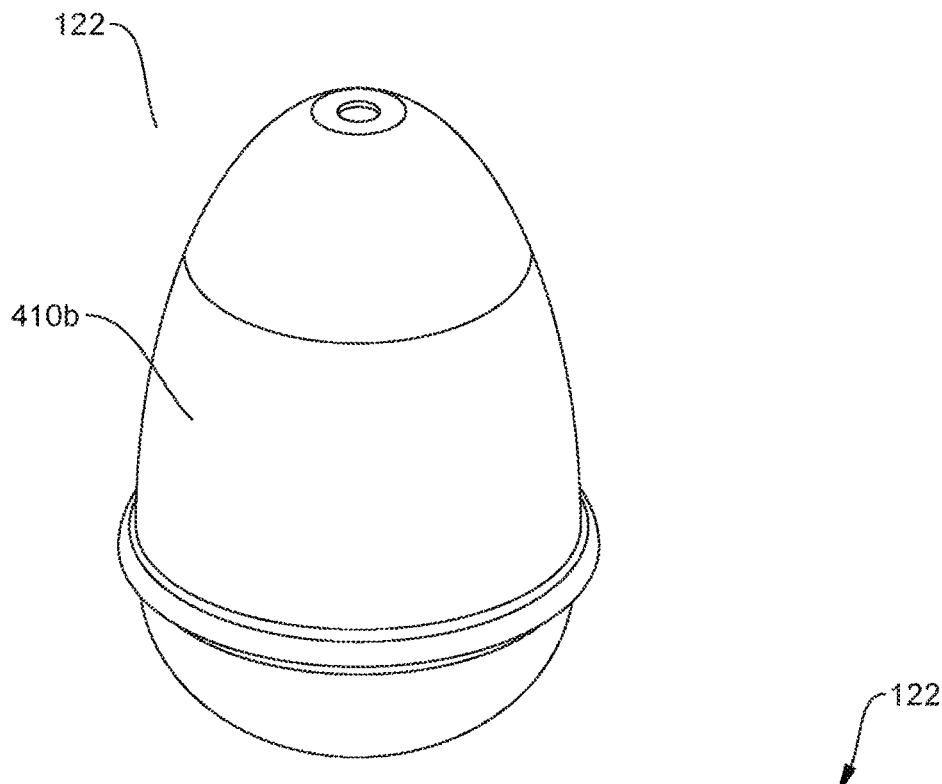
FIGS. 4A and 4B are perspective and longitudinal cross-sectional views, respectively, of one exemplary variation of a handheld user input device of an embodiment.
Figure 4B:
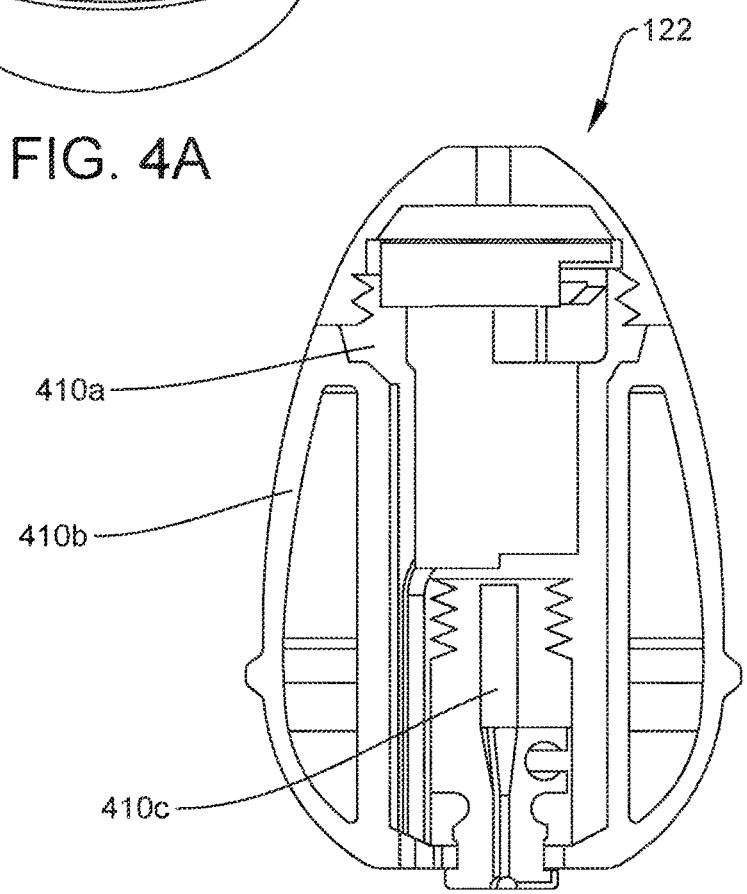

As shown generally in FIGS. 4A and 4B, an exemplary variation of a handheld user input device 122 for controlling a robotic system may include a member 410, a housing 420 at least partially disposed around the member 410 and configured to be held in the hand of a user, and a tracking sensor system 440 configured to detect at least position and/or orientation of at least a portion of the device. The housing 420 may be flexible (e.g., made of silicone). In some instances, the detected position and/or orientation of the device may be correlatable to a control of the robotic system. For example, the user input device 122 may control at least a portion of a robotic arm, an end effector or tool (e.g., graspers or jaws) coupled to a distal end of the robotic arm, a GUI, or other suitable aspect or feature of the robotic surgical system 150. Additionally, in some instances, the detected position and/or orientation of the device 122 may be correlatable to a control of a GUI. Furthermore, in some variations, the user input device 122 may include one or more sensors for detecting other manipulations of the user input device 122, such as squeezing of the housing 420 (e.g., via one or more pressure sensors, one or more capacitive sensors, etc.).

Generally, a user interface for controlling a robotic surgical system may include at least one handheld user input device 122, or may include at least two handheld user input devices 122 (e.g., a first user input device to be held by a left hand of the user, and a second user input device to be held by a right hand of the user), or any suitable number. Each user input device 122 may be configured to control one or more different aspects or features of the robotic system. For example, a user input device held in the left hand of the user may be configured to control an end effector represented on a left side of a camera view provided to the user, while a user input device held in the right hand of the user may be configured to control an end effector represented on a right side of the camera view.

In some variations, the handheld user input device 122 may be a groundless user input device configured to be held in the hand and manipulated in free space. For example, the user input device 122 may be configured to be held between the fingers of a user, and moved about freely (e.g., translated, rotated, tilted, etc.) by the user as the user moves his or her arms, hands, and/or fingers. Additionally or alternatively, the handheld user input device 122 may be a body-grounded user input device, in that the user input device 122 may be coupled to a portion of the user (e.g., to fingers, hand, and/or arms of a user) directly or via any suitable mechanism such as a glove, hand strap, sleeve, etc. Such a body-grounded user input device may still enable the user to manipulate the user input device in free space. Accordingly, in variations in which the user input device 122 is groundless or body-grounded (as opposed to permanently mounted or grounded to a fixed console or the like), the user input device 122 may be ergonomic and provide dexterous control, such as by enabling the user to control the user input device with natural body movements unencumbered by the fixed nature of a grounded system.

The handheld user input device 122 may include wired connections that, for example, may provide power to the user input device 122, carry sensor signals (e.g., from the tracking sensor assembly and/or other sensors such as a capacitive sensor, optical sensor, etc. Alternatively, the user input device may be wireless as shown in FIG. 4A and communicate commands and other signals via wireless communication such as radiofrequency signals (e.g., WiFi or short-range such as 400-500 mm range, etc.) or other suitable wireless communication protocol such as Bluetooth. Other wireless connections may be facilitated with optical reader sensors and/or cameras configured to detect optical markers on the user input device 122 infrared sensors, ultrasound sensors, or other suitable sensors.

The handheld user input device may include a clutch mechanism for switching between controlling a robotic arm or end effector and controlling a graphical user interface, etc., and/or between other control modes. One or more of the various user inputs described in further detail below may, in any suitable combination, function as a clutch. For example, touching a gesture touch region of the device, squeezing the housing, flicking or rotating the user input device, etc. may function to engage a clutch. As another example, a combination of squeezing and holding the user input device, and rotating the user input device, may function as a clutch. However, any suitable combination of gestures may function as a clutch. Additionally or alternatively, user input to other user input devices (e.g., foot pedal assembly) may, alone or in combination with user input to a handheld user input device, function as a clutch.

In some variations, engagement and disengagement of a clutch mechanism may enable transition between use of a handheld user input device as a control for the robotic system and use of the handheld user input device as a control for the GUI (e.g., to operate a cursor displayed on the screen). When a clutch mechanism is engaged such that the user input devices are used to control the GUI, positions or poses of the robotic arms may be substantially locked in place to "pause" operation of the robotic system, such that subsequent movement of the user input devices while the clutch is engaged will not inadvertently cause movement of the robotic arms.

GUI Layout

Figure 5:
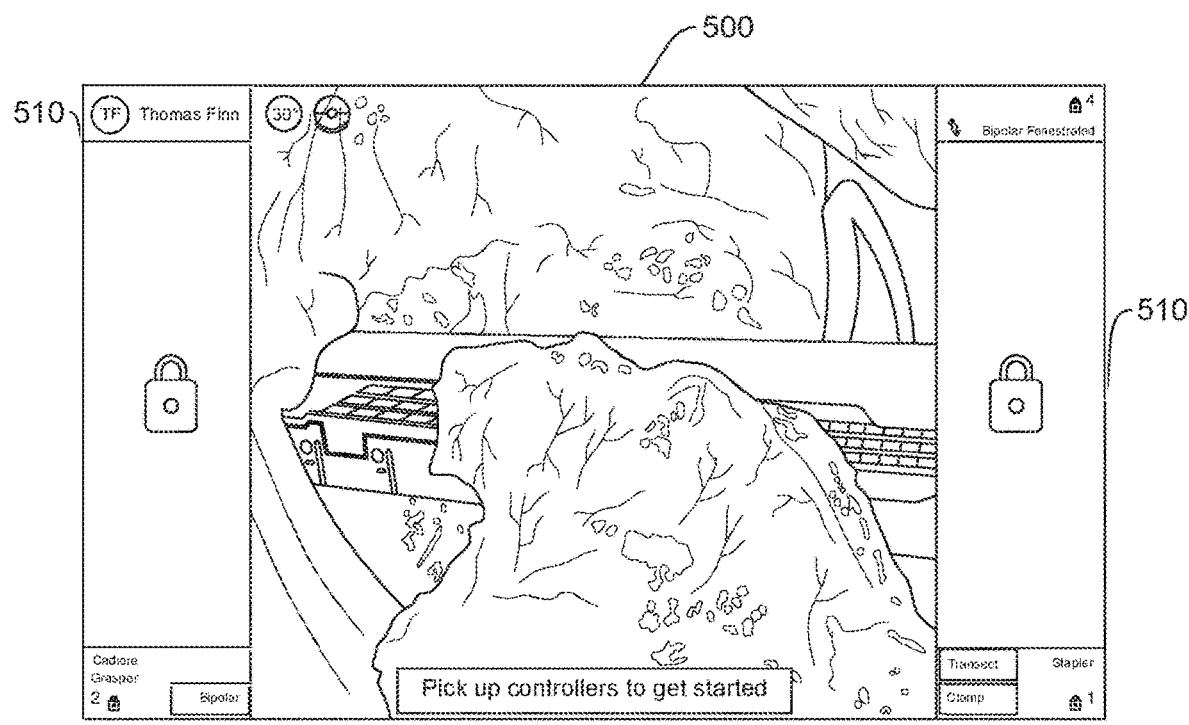
FIG. 5 is an illustration of a GUI of a robotic surgical system of an embodiment instructing a user to pick up controllers.

Any suitable layout for the GUI can be used. For example, as shown in FIG. 5, in one embodiment, the GUI comprises a first region 500 and a second region 510. Each of these regions 500, 510 can have one or more than one display area. In the example shown in FIG. 5, the first region 500 is positioned in the middle of the display, and the second regions 510 has two display areas displayed on the left and right sides of the first region 500. In this embodiment, the first region 500 displays an endoscopic view (e.g., video image or still image) of a surgical site inside a patient taken by an endoscopic camera of the robotic surgical system 150.

Figure 6:
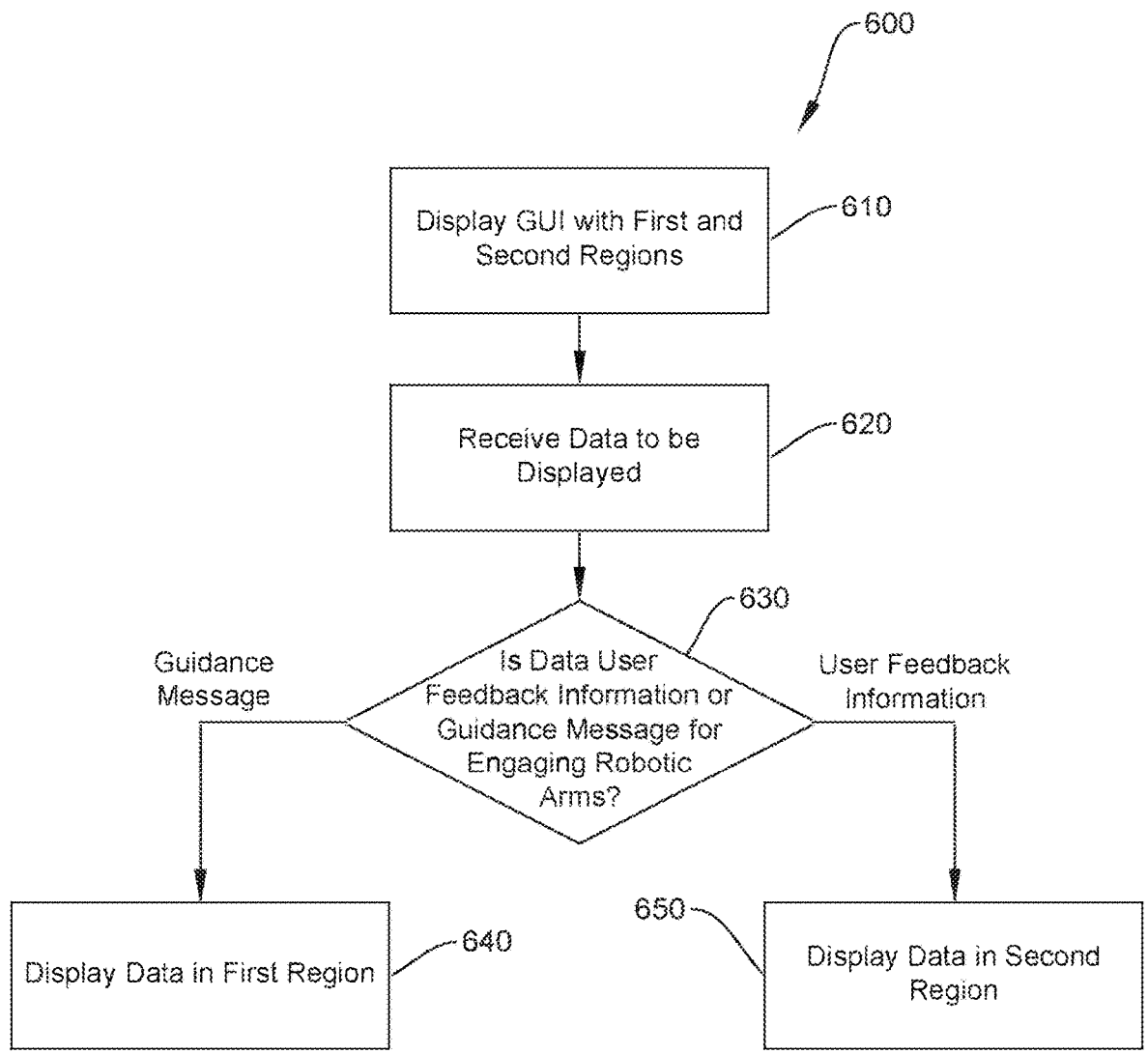
FIG. 6 is a flow chart of a method of an embodiment for displaying data on a GUI of a robotic surgical system of an embodiment.

The GUI of the robotic surgical system 150 can be used to provide information and guidance to a user. To make the GUI in this embodiment purposely simplistic and distraction free, the processor 310 of the robotic surgical system 150 determines which region 500, 510 to use to display data based on the type of data to be displayed. FIG. 6 is a flow chart 600 of a method that can be implemented by the processor 310 to do this. As shown in FIG. 6, the processor 310 (e.g., using code in the GUI module 324) displays a GUI on the display device 130, where the GUI has first and second regions 500, 510 (act 610). Next, the processor 310 receives data to be displayed on the display 130 (act 620). The data can originate from one or more applications being executed by the processor 310 or from an external location. The processor 310 then determines if the data is user feedback information or a guidance message for engaging the robotic arms 160 (act 630). If the data is a guidance message for engaging the robotic arms 160, the processor 130 displays the data in the first region 500 by overlaying the guidance message on top of the endoscopic view of the surgical site in the first region 500 (act 640). However, if the data is user feedback information, the processor 310 displays the data in the second region 510 (act 650). The following paragraphs and accompanying drawings will now be discussed to illustrate this embodiment.

Returning to FIG. 5, the first region 500 displays an endoscopic view of a surgical site inside a patient taken by an endoscopic camera of the robotic surgical system 150. This view typically shows patient tissue and end effector(s) of the robotic arm(s). The second region 510 (here, left and right side panels) are available for display of user feedback information, such as, but not limited to, errors, warning, alerts, and notifications. For example, in this illustration, the upper portion of the left-hand side of the second region 510 shows the initials of the user who is logged into the robotic surgical system 150, the type of scope used (here, a 30 degree scope pointed upward), and a horizon line indicator. The other corners of the second region 510 display messages indicating the tools that are on three of the robotic arms (here, grasper, bipolar fenestrated, and stapler scissors).

As noted above, in this embodiment, the robotic surgical system 150 determines whether to display data in the first region 500 or the second region 510 depending on the type of data to be displayed. In one embodiment, the messages overlaid on top of the image of the surgical site in the first region 50 are only guidance messages that provide user instructions for the surgeon to engage the robotic arms 160. As used herein, a robotic arm is "engaged" when movement of at least one of the plurality of user input devices is translated in real time to movement of an end effector of the robotic arm. Since the surgeon will usually be focused on the image of the surgical site in the first region 50, overlaying guidance messages on the image of the surgical site in the first region 500 is likely get the surgeon's attention. Having user feedback information displayed in the second region 510 (and not over the image of the surgical site in the first region 500) avoids distracting the surgeon during surgery (minimizing cognitive load), allowing the surgeon to focus on the surgical procedure and not the GUI. If and when the surgeon wants to view the user feedback information, he can by glancing at the second region 510. With this layout, the surgeon can focus on the procedure and patient because the display is clean and noise is reduced.

In the example shown in FIG. 5, the guidance message "Pick up controllers to get started" is overlaid on the image of the surgical site in the first region 500, instructing the surgeon to pick up the handheld left and right user input devices 122 (the handheld devices 122 are used to illustrate this example, but it should be understood that other types of user input devices can be used). This can occur, for example, when the surgeon first sits down at the user console 100 or after the surgeon puts down or drops the user input devices 122. In one embodiment, one of the foot controls acts as a "clutch pedal," which can toggle the functionality of the user input devices 122 between controlling the robotic arms and controlling the graphical user interface.

Figure 7:
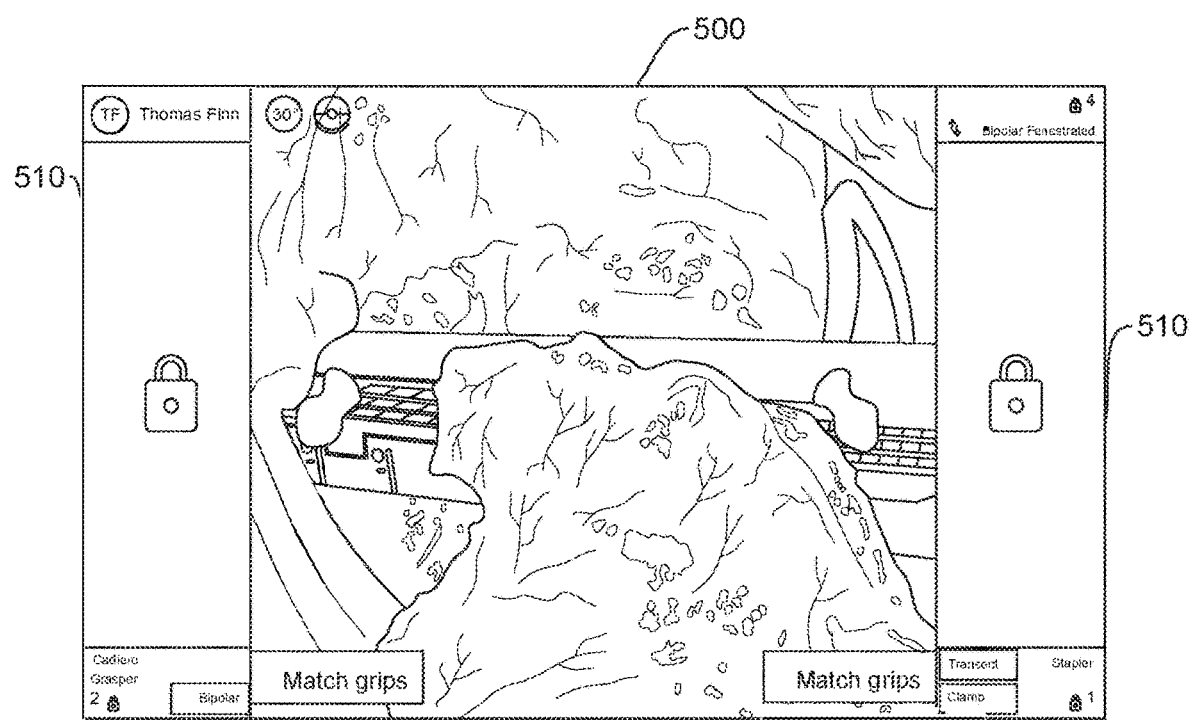
FIG. 7 is an illustration of a GUI of a robotic surgical system of an embodiment instructing a user to match grips.

After the surgeon picks up the handheld left and right user input devices 122, the message overlaid on the image of the surgical site in the first region 500 changes to "Match Grips," as shown in FIG. 7. "Match Grips" instructs the surgeon to open and close the controller's grip to match the current state of the instrument (e.g., the grip angle of the end effector). After the surgeon "matches grips," he fully engages the robotic arms and can proceed with surgery.

Figure 8A:
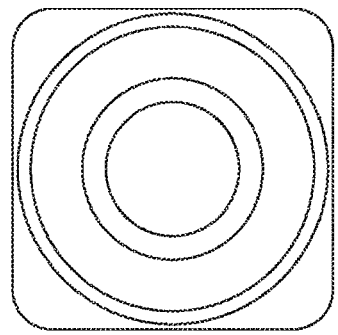
FIGS. 8A-8F are illustrations of various graphical tools of an embodiment that can be used to instruct a user to match grips.
Figure 8B:
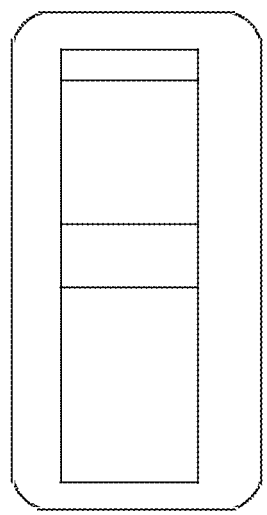
Figure 8C:
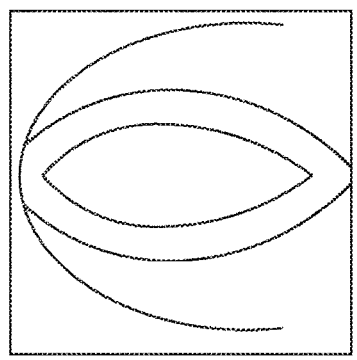
Figure 8D:
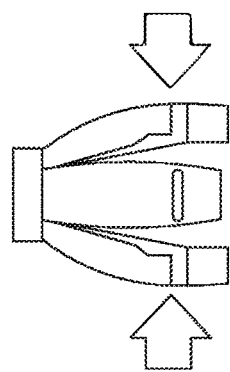
Figure 8E:
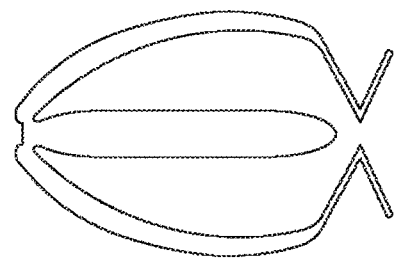
Figure 8F:
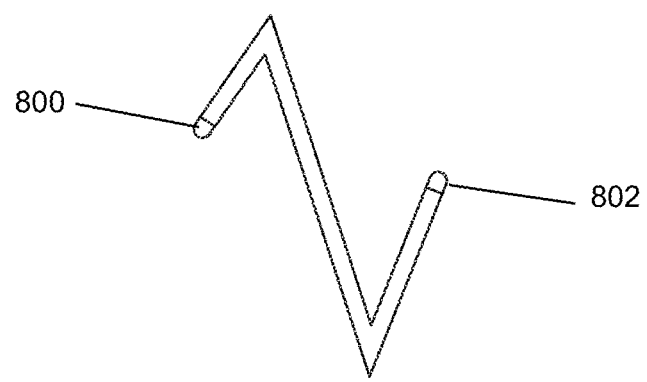

Various aids can be used to assist the surgeon in matching grips. For example, as shown in FIG. 7, icons of the left and right user input devices 122 are also overlaid on the image of the surgical site. As the surgeon opens and closes each controller's grip, the color of the icons can change to provide feedback to the surgeon if he needs to provide a tighter or looser grip to align his grip with the state of the instrument. Other ways for providing feedback on "match grips" to the surgeon can be provided. For example, FIGS. 8A-8F are illustration of various graphical tools that can be used to instruct a user to match grips. In FIG. 8A, the grip to match is represented by the inner circle, and the outer circle represents the current grip of the user input device. As the user grips the user input device tighter, the outer circle will move closer to the inner circle. In FIG. 8B, the grip to match is represented by the middle bar, and the upper bar represents the current grip of the user input device. As the user grips the user input device tighter, upper bar will move closer to the middle bar. In FIG. 8C, the grip to match is represented by the inner shape, and the outer shape represents the current grip of the user input device. As the user grips the user input device tighter, the outer shape will form closer to the inner shape. In FIG. 8D, a representation of the physical shape of the user input device is shown, with arrows representing pressing or releasing the user input device grip. In FIG. 8E, the jaws of the user input device represent the actual state of the user input device, and the line path indicates the squeeze amount of the UID to match grips. In FIG. 8F, the left dot 800 represents the state of the user input device, and the right dot 802 represents the state of the end effector. The path between the dots indicates the steps the user input device needs to go through.

Figure 9:
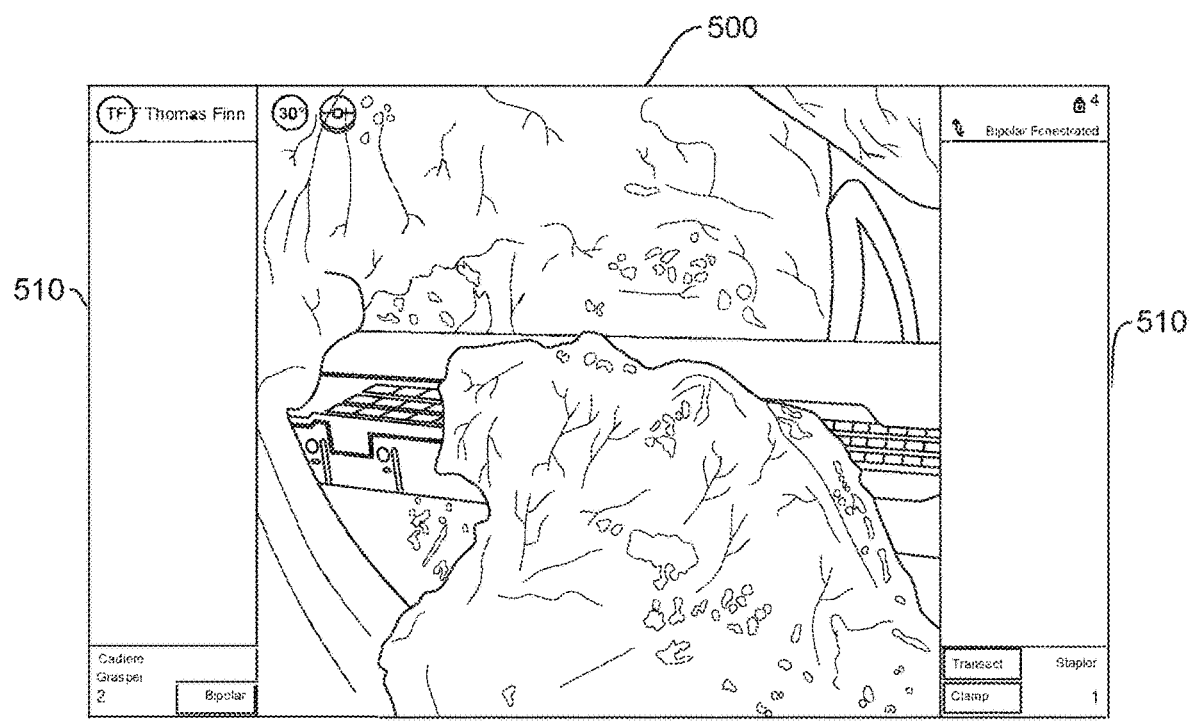
FIG. 9 is an illustration of a GUI of a robotic surgical system of an embodiment.
Figure 10:
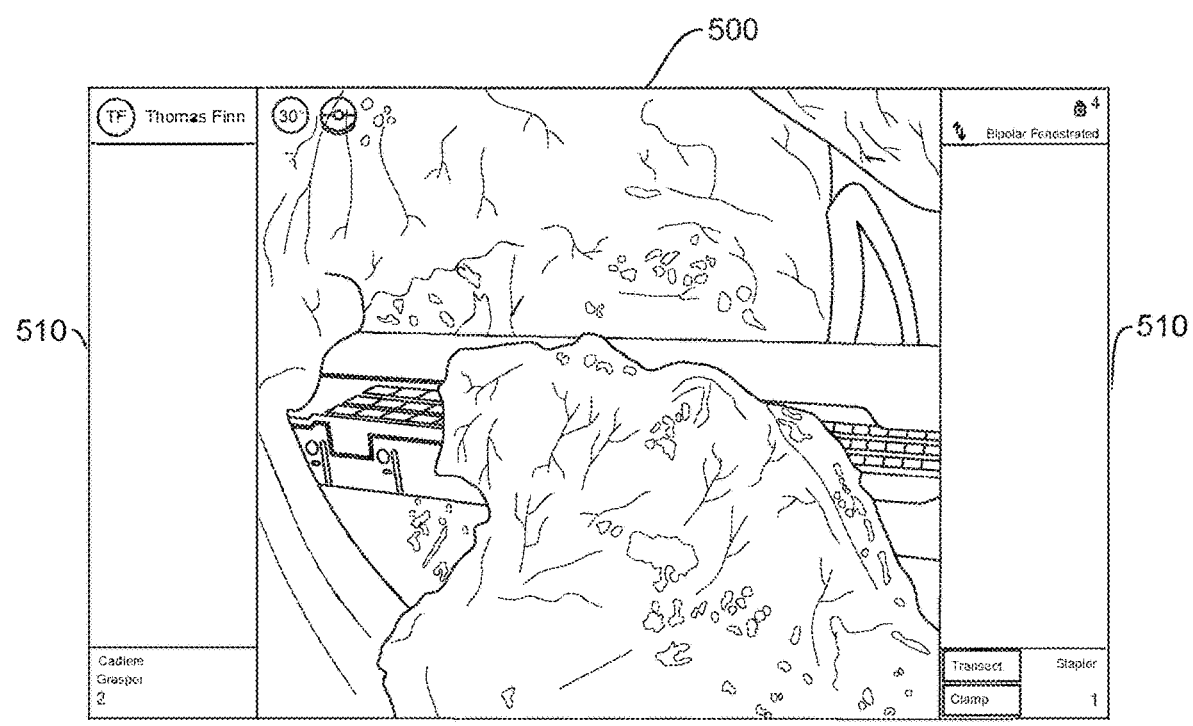
FIG. 10 is an illustration of a GUI of a robotic surgical system of an embodiment that shows a hover indicator when a user hovers his foot over a pedal.
Figure 11:
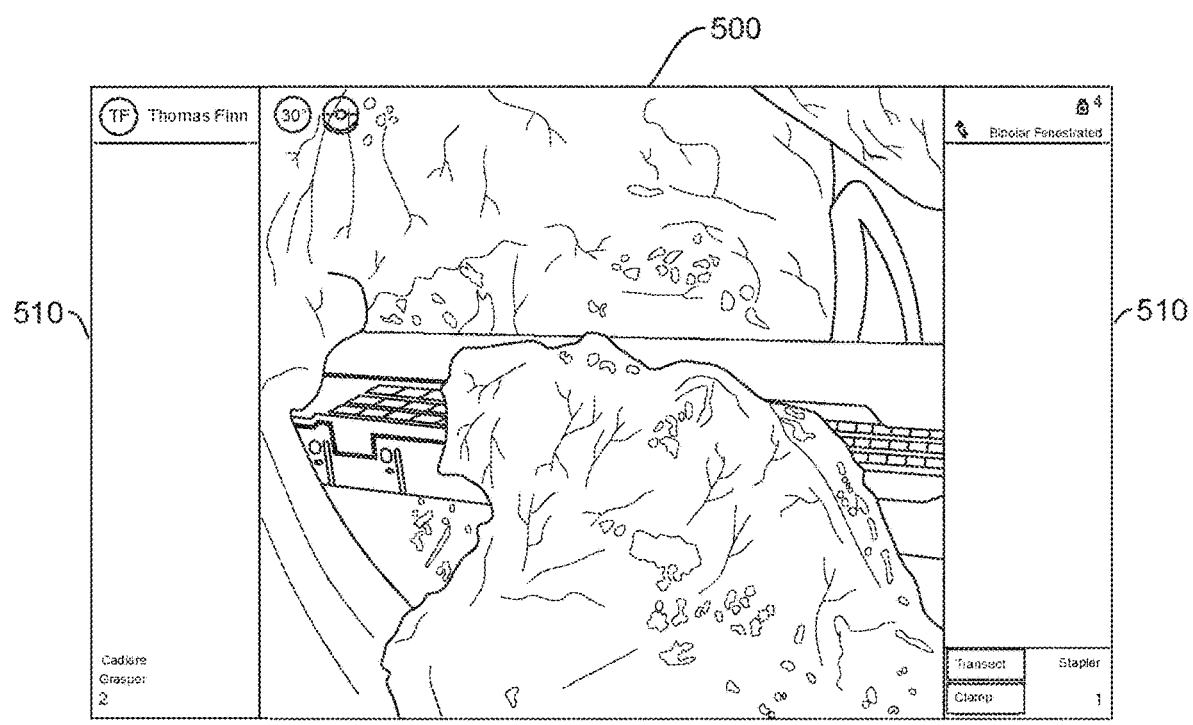
FIG. 11 is an illustration of a GUI of a robotic surgical system of an embodiment that shows an energy activation indicator when a user presses an energy pedal.

Once the surgeon matches the grips of the left and right user input devices 122 to the current state of the instrument, the surgeon has successfully engaged the robotic arms and can manipulate the left and right user input devices 122 to perform surgery on the patient. During surgery, the graphical user interface can present feedback information to the surgeon in the second region 510 in a timely, perceptible, but un-intrusive way. For example, as shown in FIG. 9, the lower right portion of the second region 510 shows "cut" and "coagulation" bars that are "lit up," indicating that this tool is active. These bars are color-coded to the pedals 120 of the robotic surgical system 150, and the length of the bars indicate the amount of energy applied to the tool by the pedals 120. The long "cut" bar in FIG. 10 is a hover indicator. In this embodiment, the pedals 120 have a hover sensor when the surgeon's foot is over but not pressing the pedal 120. The hover indicator can be pulsing or animated to catch the surgeon's attention. This is a safety feature, as it may be desirable to make the hover indicator noticeable before the surgeon actually presses the pedal 120. As shown in FIG. 11, when the pedal 120 is pushed and cut energy is applied, the full tool kit is filled with yellow color, showing the type and level of energy.

Figure 12:
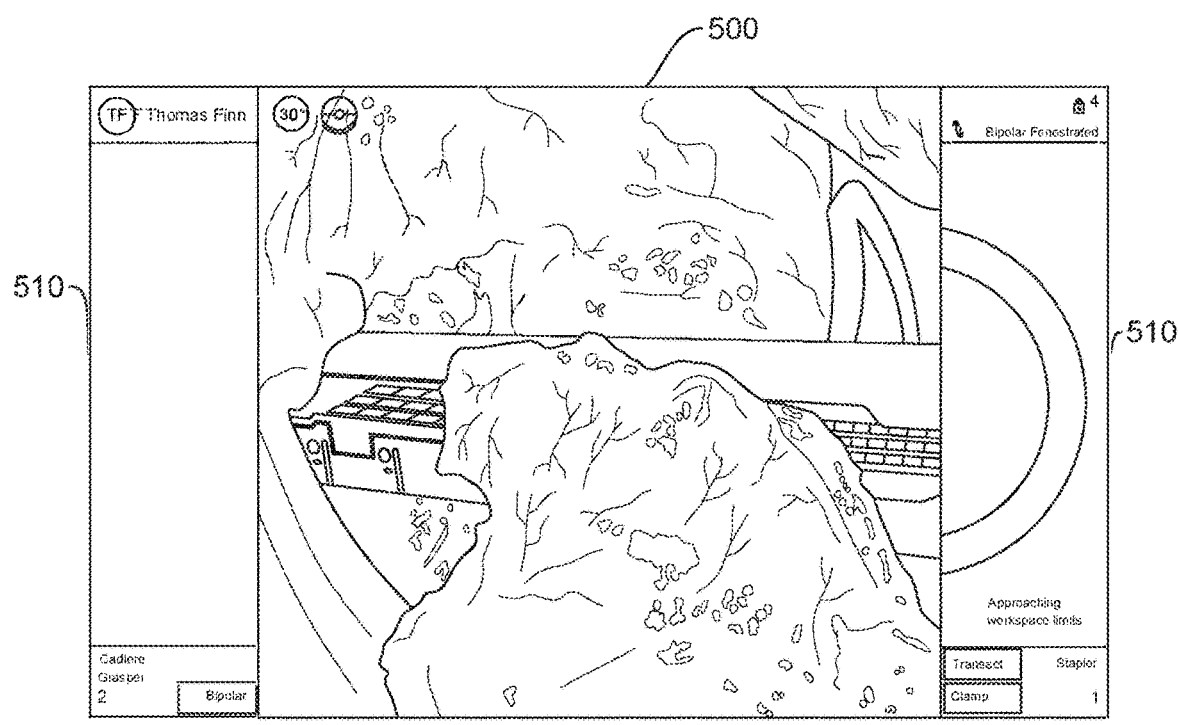
FIG. 12 is an illustration of a GUI of a robotic surgical system of an embodiment displaying a notification of an approaching workspace limit.
Figure 13:
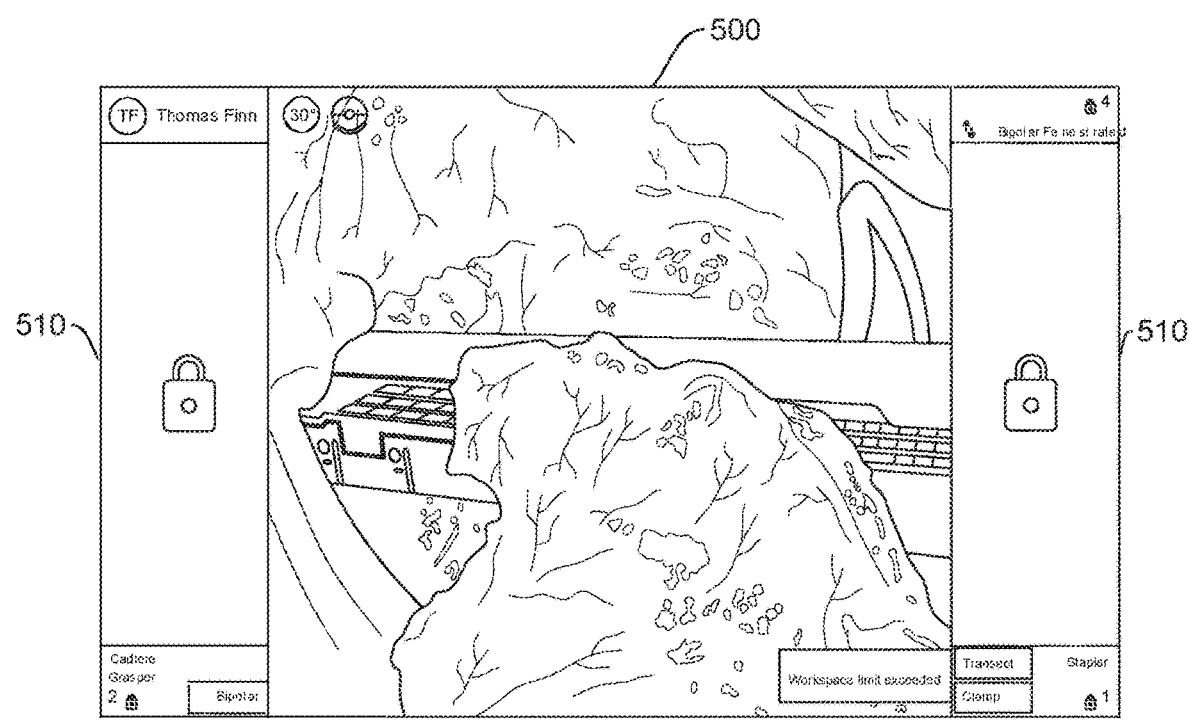
FIG. 13 is an illustration of a GUI of a robotic surgical system of an embodiment displaying a notification that a workspace limit has been exceeded.

FIGS. 12 and 13 are examples of when the user feedback information displayed in the second region 510 relates to the position of the user input devices 122. In one embodiment, the robotic surgical system 150 uses an electromagnetic tracker to track the position of the user input devices 122. The space within which the user input devices 122 can operate is defined by a boundary (e.g., a cube), and the system 150 defines a buffer zone around the edges of the boundary. When the surgeon moves the user input devices 122 into the buffer zone, the robotic surgical system 150 displays a message in the second region 510 to inform the surgeon that he is close to exceeding the workspace limit. This is shown in FIG. 12. As shown in that figure, the right-hand side of the second region 510 shows a user feedback message informing the surgeon that he is approaching the workspace limit of the right user input devices. The message is displayed on the right-hand side of the second region 510 because the message relates to the right user input device. If the message related to the left user input device, the message could be displayed on the left-hand side of the second region 510.

The circle displayed around the message provides an indication of how close the user input devices 122 are to exceeding the limit. As the user approaches the workspace limit, larger circles can be added. Many alternative graphics can be used. For example, instead of growing circles, a line/bar can be used. Also, the origin of the circle can be positioned near the edge of the second region 510 that corresponds to the location of the limit that the user is approaching (e.g., the bottom of the second region 510 if the user is approaching a lower-edge workspace limit). Various graphics and/or animation can be used.

As shown in FIG. 13, if the limit is exceeded, the robotic surgical system 150 displays a message in the second region 510 (now completely in blue) informing him of such and how to reposition the user input device to re-engage the robotic arm). After the surgeon moves the user input device back into the workspace, the surgeon would tap the clutch pedal and repeat the match grips process described above.

Figure 14:
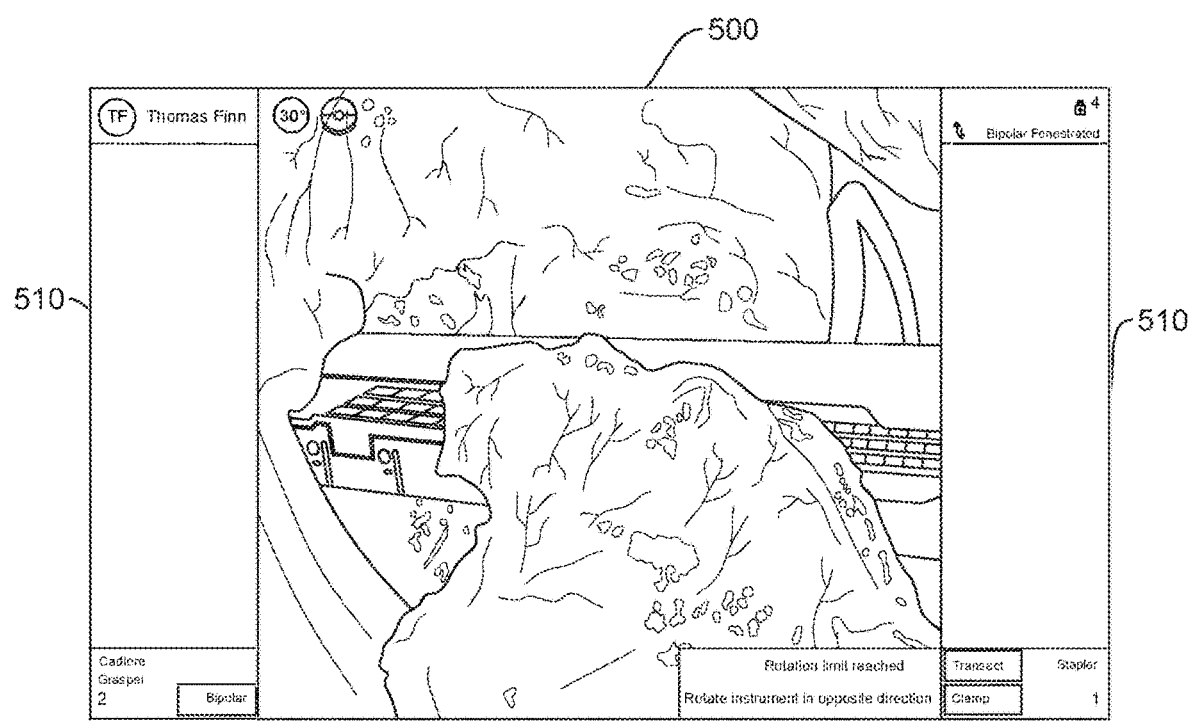
FIG. 14 is an illustration of a GUI of a robotic surgical system of an embodiment displaying a notification that a rotation limit has been reached.
Figure 15:
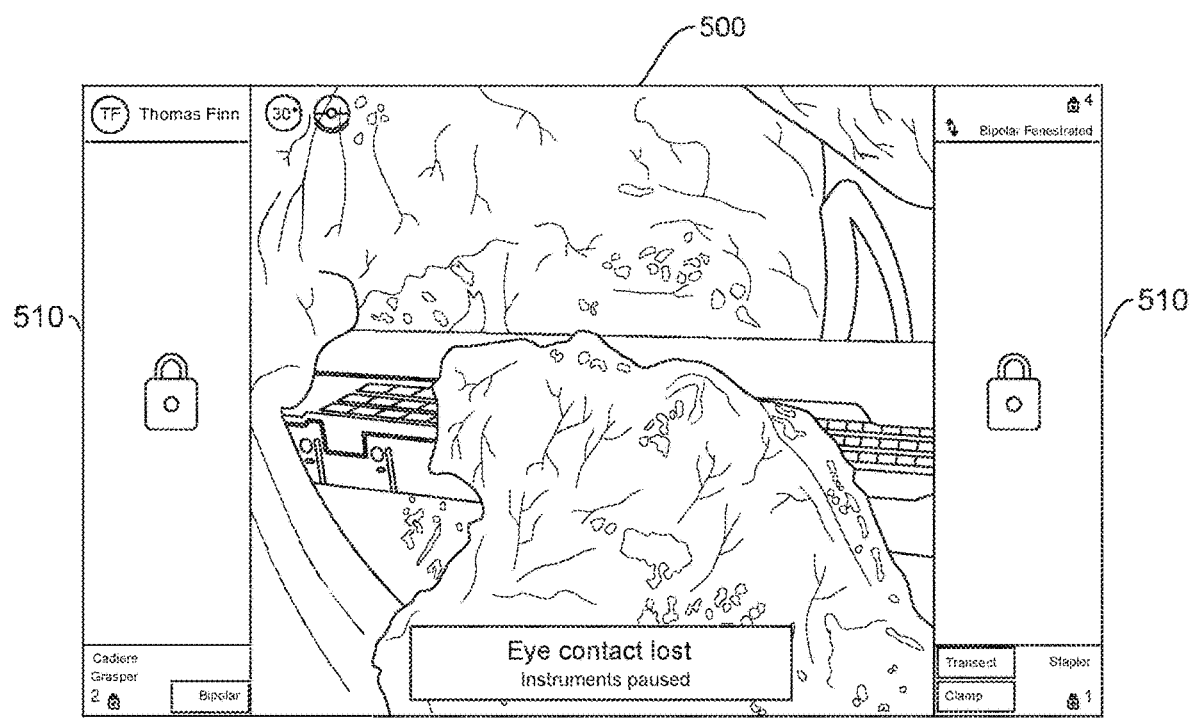
FIG. 15 is an illustration of a GUI of a robotic surgical system of an embodiment displaying a notification that eye contact has been lost.

FIG. 14 illustrates the message that is displayed in the second region 510 when the surgeon rotates the end effector too much. As shown in FIG. 14, the message instructs the surgeon to rotate the user input device in the opposite direction (again, the message is on the right-hand side of the second region 510 because the message relates to the right user input device). FIG. 14 shows that the message in one embodiment is in high contrast (here, white on black) to catch the attention of the surgeon, while still not distracting from the surgical view in the first region 500. It may also be desired to provide blank space around the message, both to avoid cluttering the message area and to provide room for translations in other languages where the translation might be longer than the English-language message.

In some implementations, the robotic surgical system 150 has an eye sensor on the user console/surgeon bridge 100 to sense whether or not the surgeon is looking at the display screen 130. If the surgeon is not looking at the display screen 130, the surgeon may not be focused on the surgical site, and movement of the user input devices can cause movement of the robotic arms that can harm the patient. So, when the robotic surgical system 150 detects that eye contact has been lost, the robotic surgical system 150 pauses operations of the instruments, and displays a message to that effect in the second region 510 (here, on both the left- and right-hand sides to indicate that eye contact has been lost on both eyes).

Figure 16:
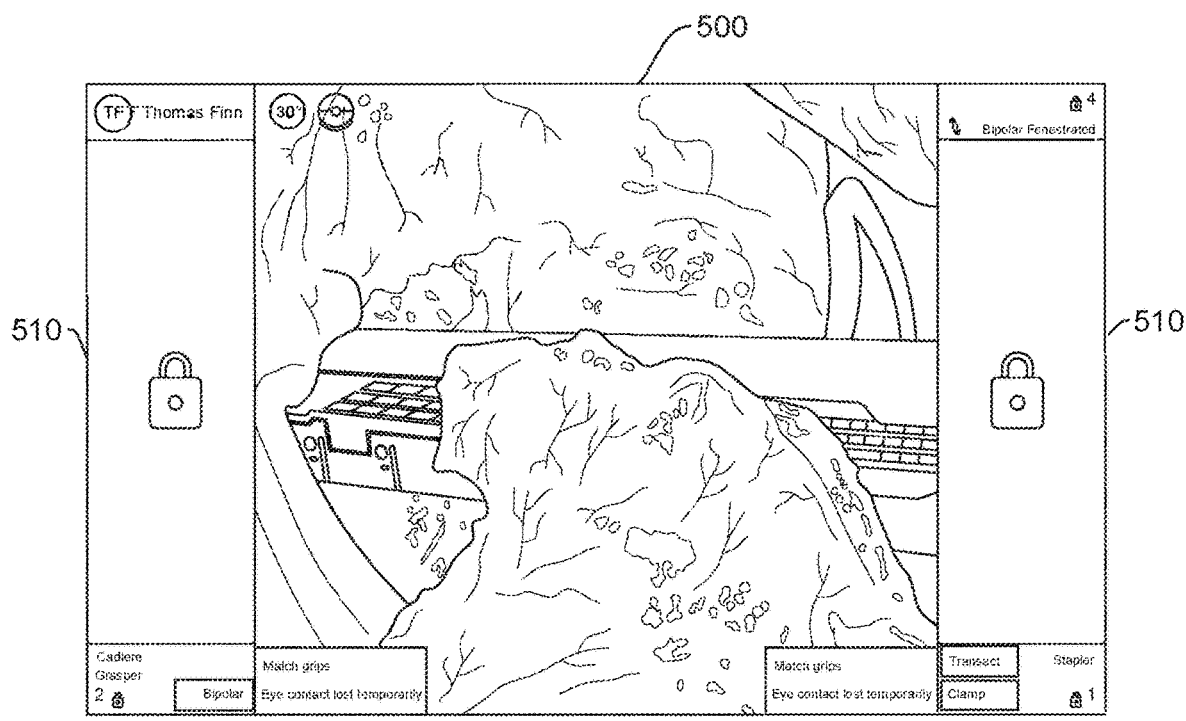
FIG. 16 is an illustration of a GUI of a robotic surgical system of an embodiment instructing a user to match grips after eye contact has been lost temporarily.
Figure 17:
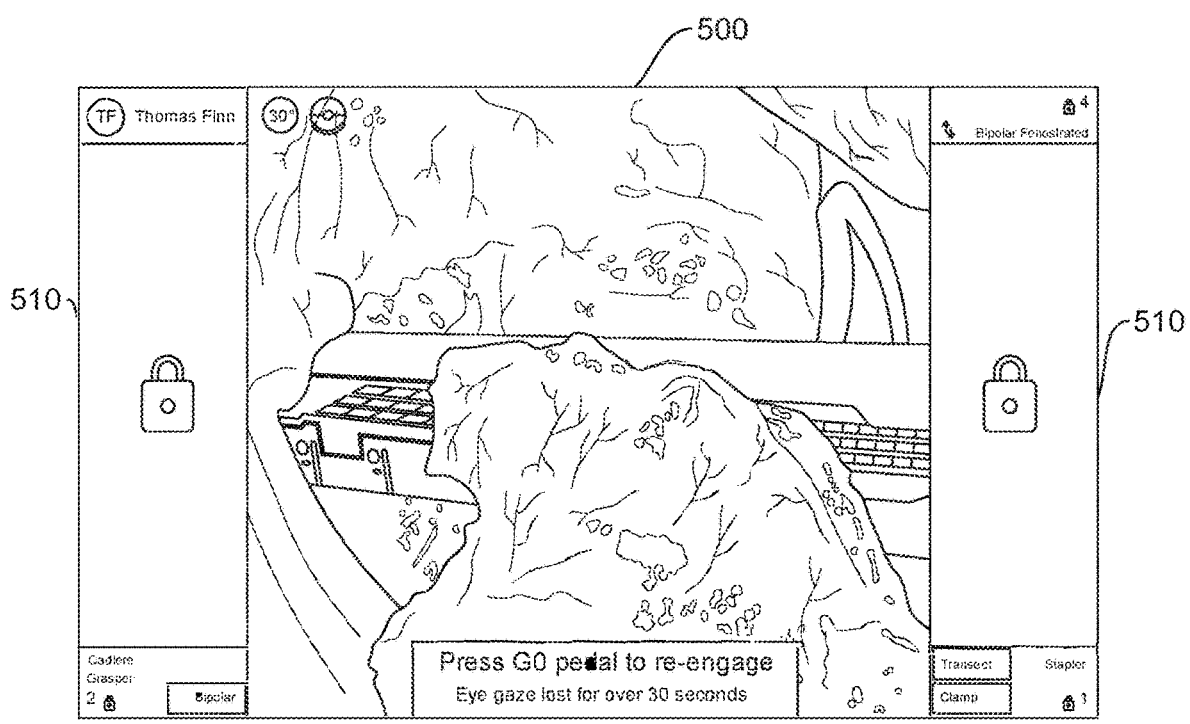
FIG. 17 is an illustration of a GUI of a robotic surgical system of an embodiment instructing a user to match grips after eye contact has been lost for over thirty seconds.

After eye contact is re-established, the surgeon needs to re-engage with the robotic surgical system 150. In one implementation, the actions needed depend on whether the loss of eye contact was temporarily or not (e.g., less than thirty seconds, or thirty seconds or more). If the loss of eye contact was temporarily, the robotic surgical system 150 displays a message over the image of the surgical site in the first region 500 instructing the surgeon to match grips (FIG. 16). Once the grips have been matched, the surgeon has re-engaged with the robotic surgical system 150 and can proceed with surgery. However, if the loss of eye contact was over five seconds in this example, the robotic surgical system 150 displays a message over the image of the surgical site in the first region 500 instructing the surgeon to tap the clutch pedal (FIG. 17), after which the robotic surgical system 150 will display a message over the image of the surgical site in the first region 500 instructing the surgeon to match grips.

Figure 18:
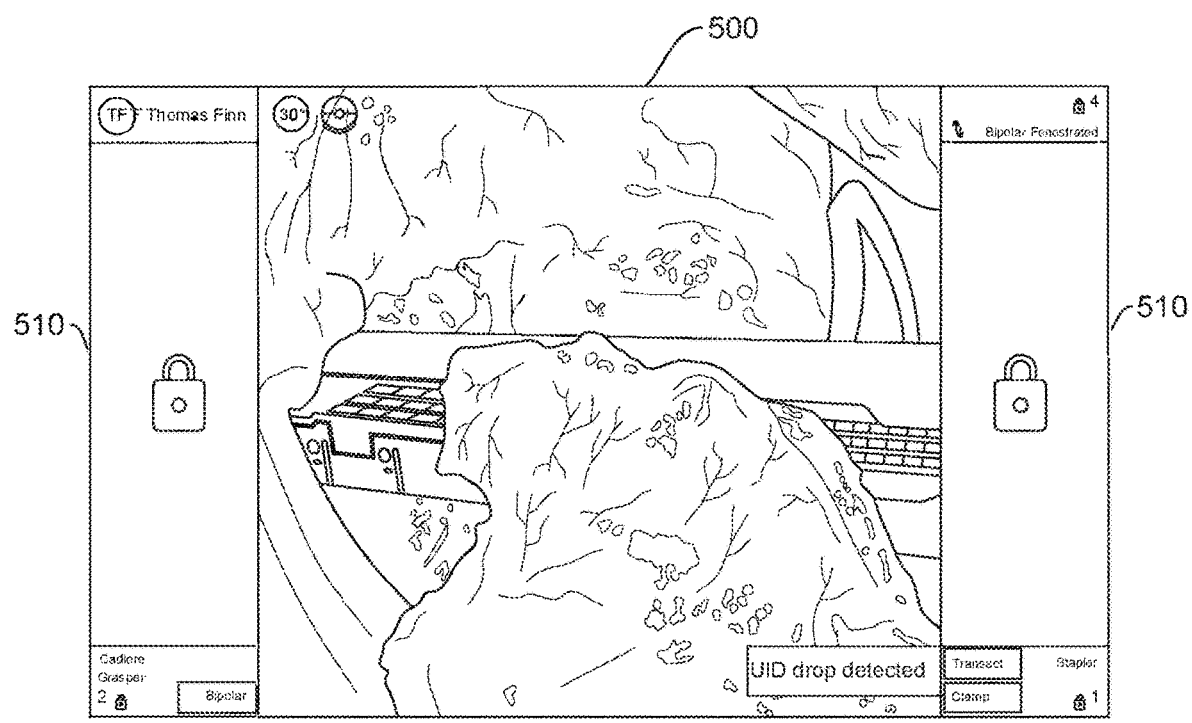
FIG. 18 is an illustration of a GUI of a robotic surgical system of an embodiment displaying a notification that a user input device has been dropped.
Figure 19:
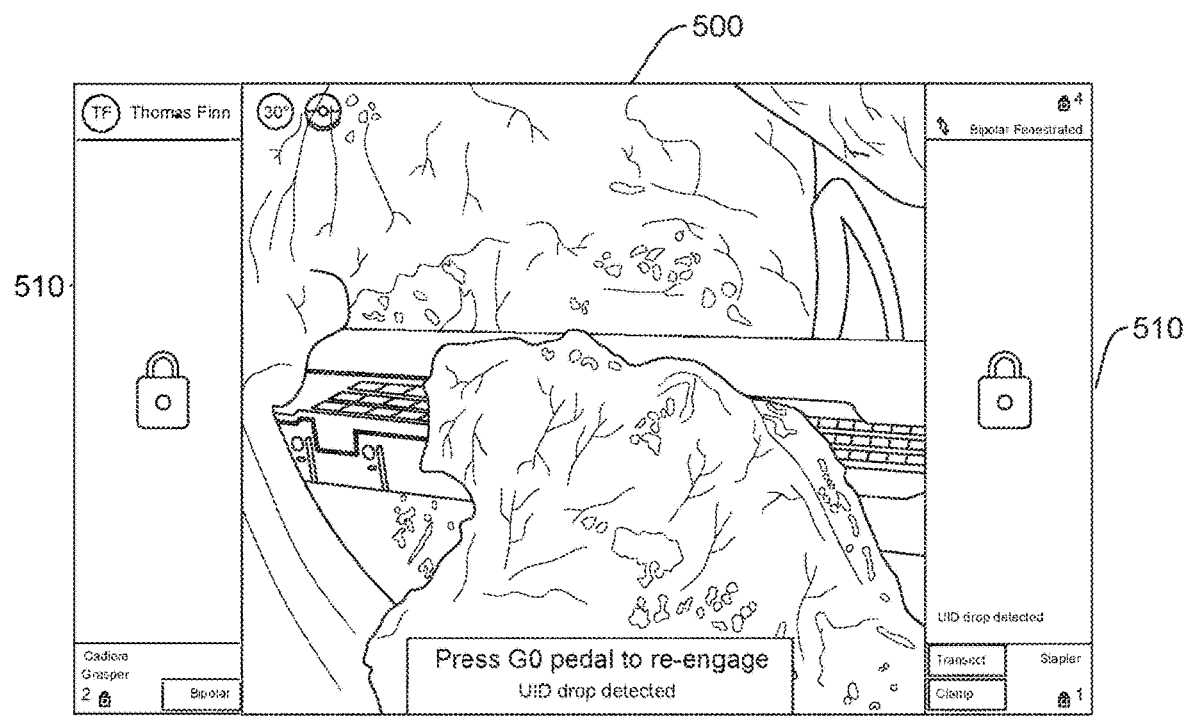
FIG. 19 is an illustration of a GUI of a robotic surgical system of an embodiment instructing a user to tap a clutch pedal after a user input device has been dropped.

Some messages displayed in the second region 510 may be more important than others, and the robotic surgical system 150 can use different ways to indicate the importance of a message. For example, as shown in FIG. 18, in one embodiment, when the surgeon drops a user input device, the robotic surgical system 150 displays a message with a red background in the second display region 510 informing the surgeon that the user input device has been dropped and that it needs to be picked up to continue. Once the surgeon picks up the dropped user input device, the robotic surgical system 150 displays a message over the image of the surgical site in the first region 500 instructing the surgeon to tap the clutch pedal (FIG. 19), after which the robotic surgical system 150 will display a message over the image of the surgical site in the first region 500 instructing the surgeon to match grips.

Figure 20:
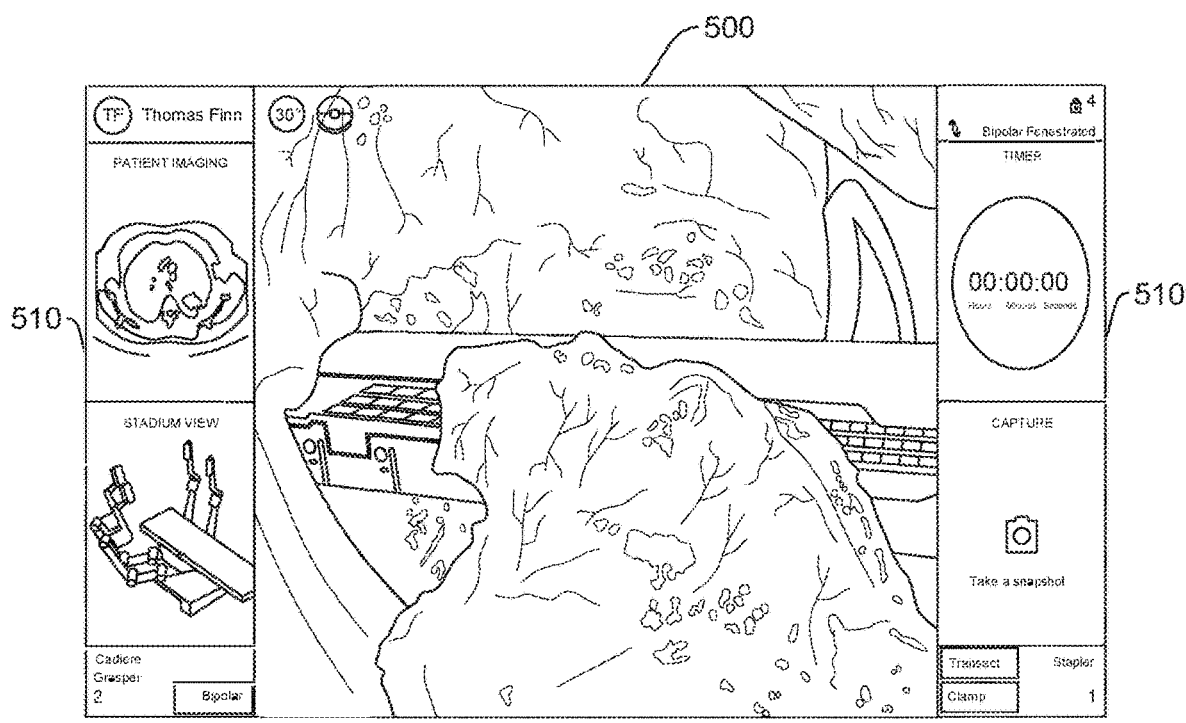
FIGS. 20-23 are illustrations of a GUI of a robotic surgical system of an embodiment that displays applications in display areas of a second region of the GUI.

In one embodiment, the second region 510 can be also used for purposes other than for displaying messages. For example, as shown in FIGS. 20-23, the second region 510 can be used to display one or more apps running on the robotic surgical system 150. FIG. 20 shows several apps in the second region 510. The layout and location of the apps can be chosen in any suitable manner and can be reconfigurable. In the example shown in FIG. 20, the upper left-hand corner of the second region 510 contains an image view application that is in communication with a medical records database or other suitable repository such that the image viewer application may receive medical images relating to the surgical procedure. For example, the image viewer application may receive and display pre-operative images (e.g., X-ray, CT, MRI, ultrasound, etc.) of the patient. Such display of pre-operative images may allow a surgeon and/or other user(s) to easily view pre-operative images before, during, and/or after a surgical procedure and may help the surgical team make better, more informed decisions relating to the surgical procedure. The lower left-hand corner of the second region 510 contains a procedure template application that can be used to generate a list of items relating to performance of a surgical procedure. For example, the procedure template application may display a checklist of surgical tasks that are part of a surgical procedure, a list of equipment or tools needed for the surgical procedure, a list of operating room setup tasks, a schematic diagram of port location and arm/surgical instrument setup, etc. The upper right-hand corner of the second region 510 contains a timer application that can, for example, track duration of the surgical procedure and/or duration of segments of the surgical procedure (e.g., individual surgical tasks and other tasks performed, and/or groups thereof). Other types of apps and embodiments can be used, such as those described in "Multi-Panel Graphical User Interface for a Robotic Surgical System," U.S. patent application Ser. No. 15/842,485, filed Dec. 14, 2017, which is hereby incorporated by reference.

Figure 21:
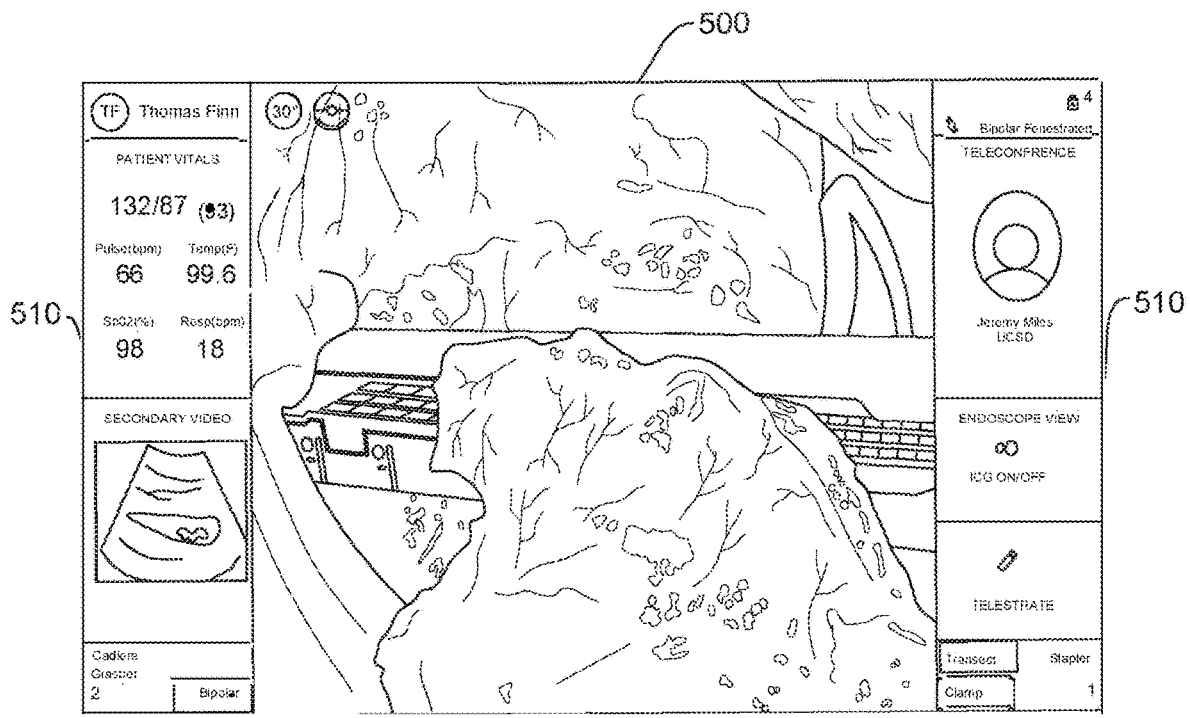
Figure 22:
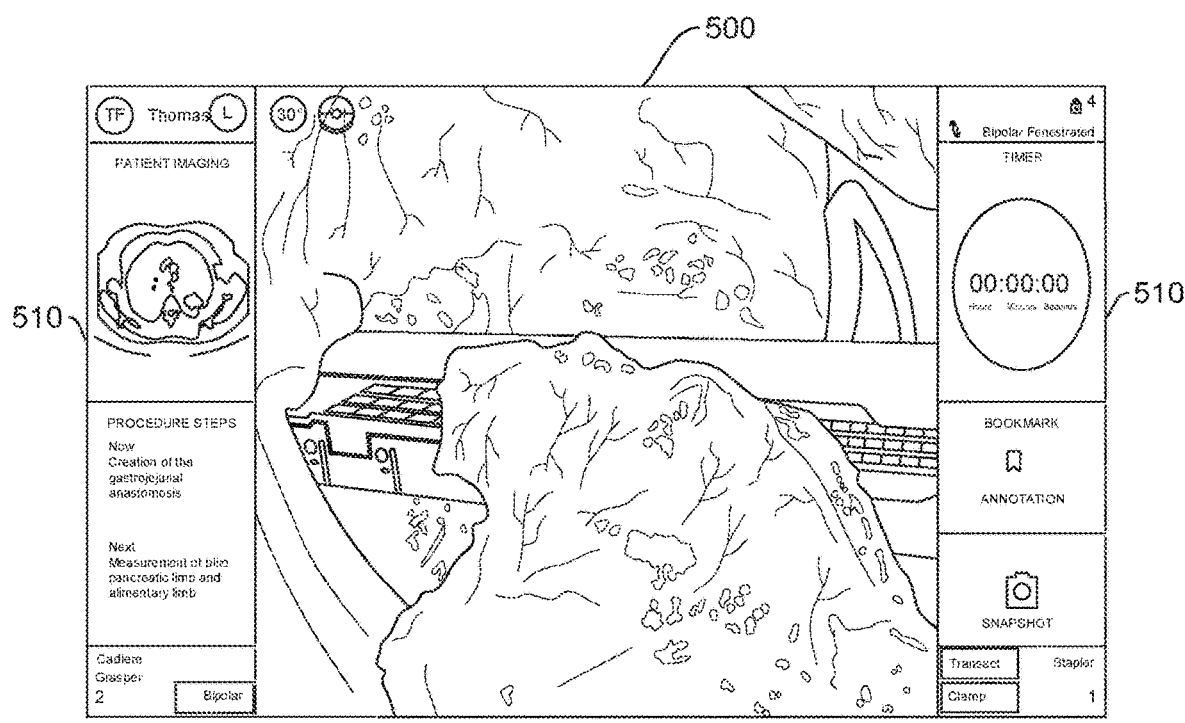
Figure 23:
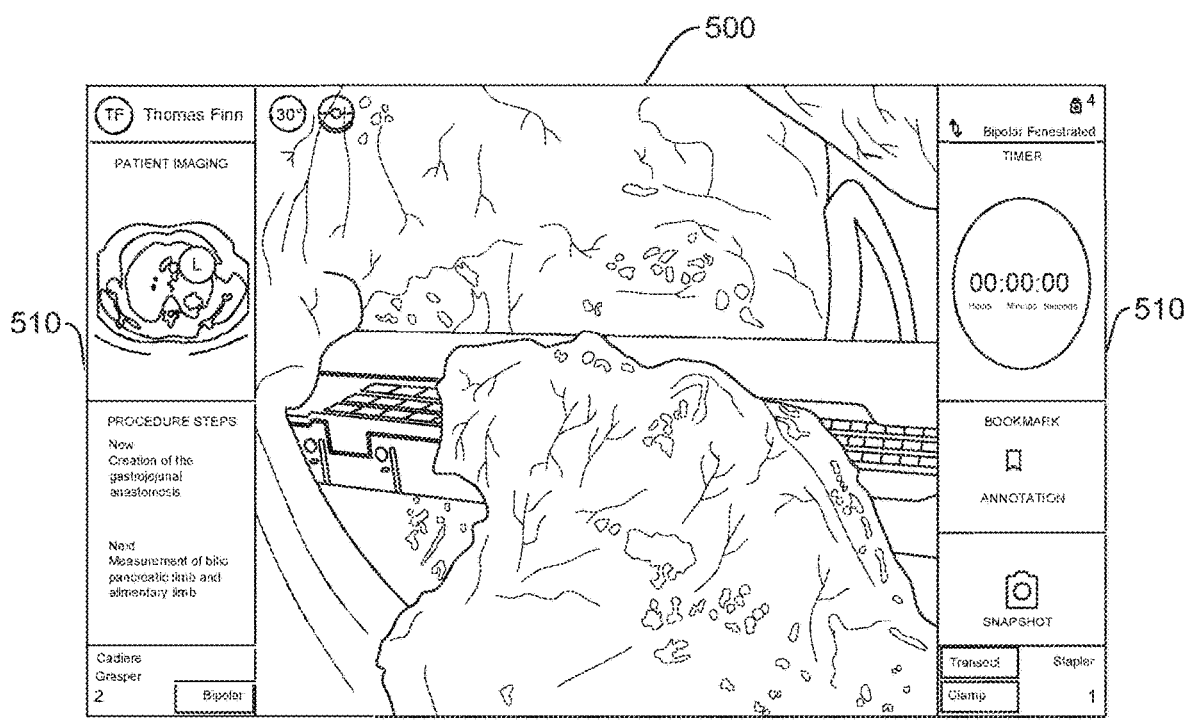

The user input devices 122 can be used to toggle among the various displays and apps. For example, in one embodiment, the display in FIG. 20 is the result of the surgeon pressing the clutch pedal and squeezing both user input devices 122, the display in FIG. 21 is the result of the surgeon squeezing both user input devices 122 again, and the displays in FIG. 22 and FIG. 23 are the result of hovering the user input devices 122 over various portions of the display. In one embodiment, the border of the display area over which a cursor is hovering is highlighted to indicate which display area is active.

Figure 24:
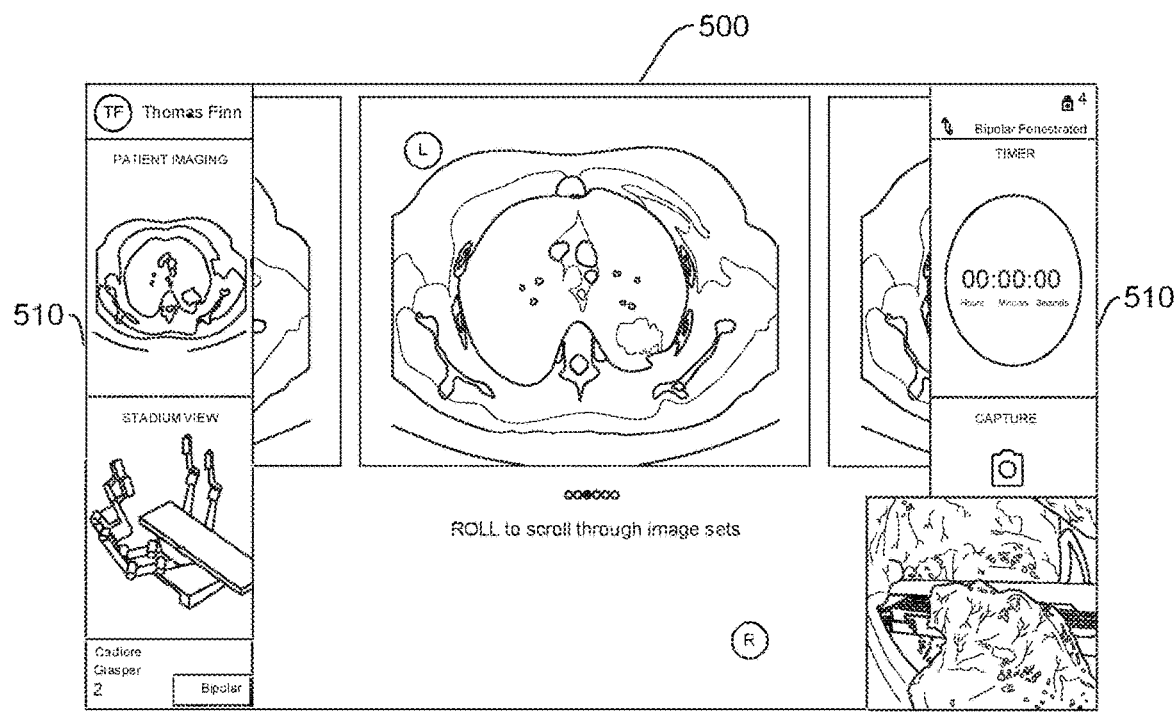
FIGS. 24-25 are illustrations of a GUI of a robotic surgical system of an embodiment in which a CT image is displayed in a first region of the GUI.
Figure 25:
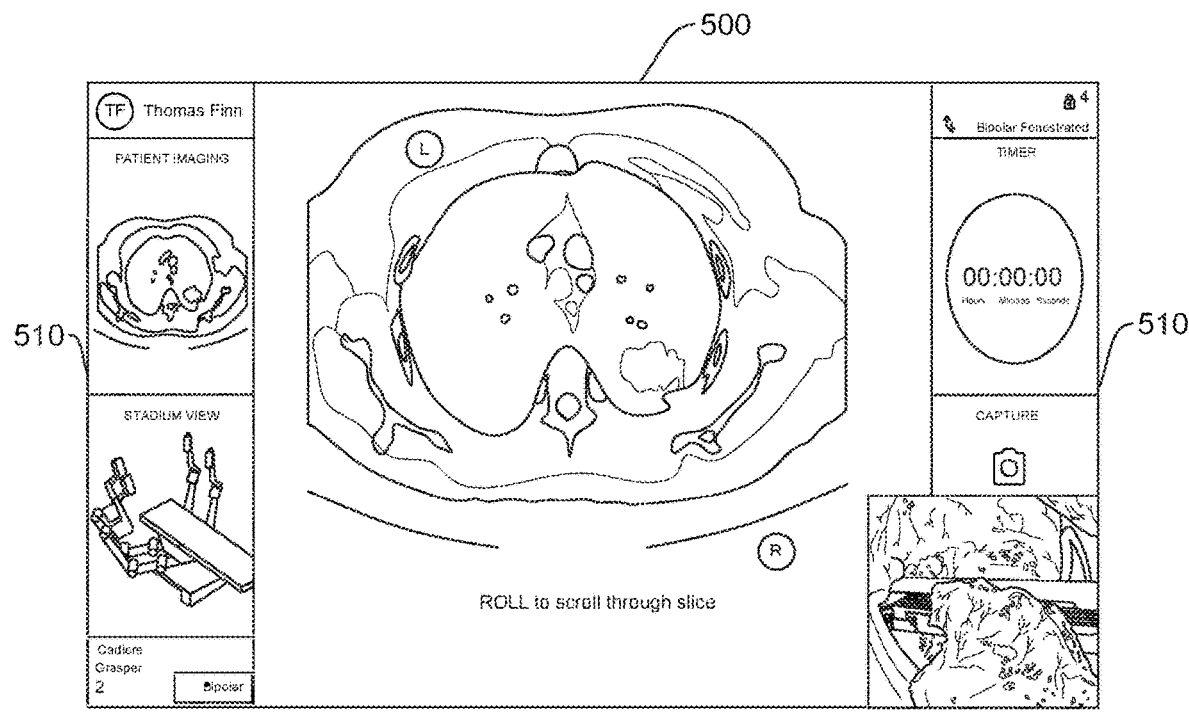
Figure 26:
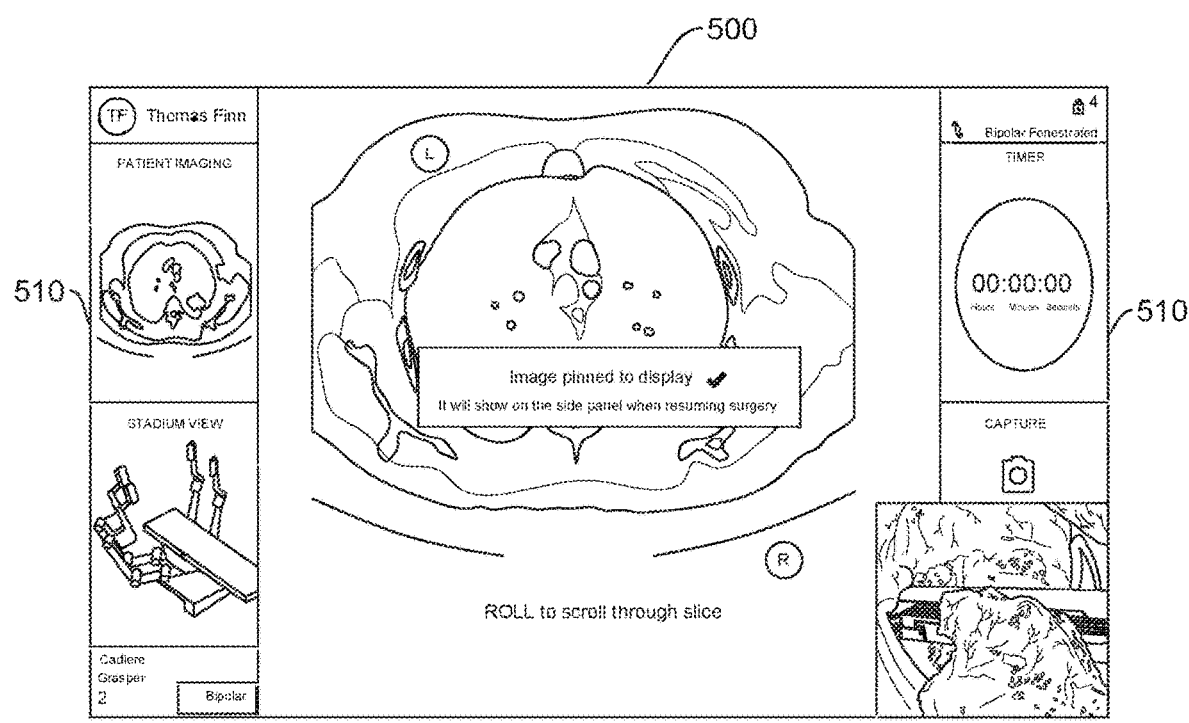
FIG. 26 is an illustration of a GUI of a robotic surgical system of an embodiment in which a user instructs the robotic surgical system to pin a CT image to a display area in a second region.
Figure 27:
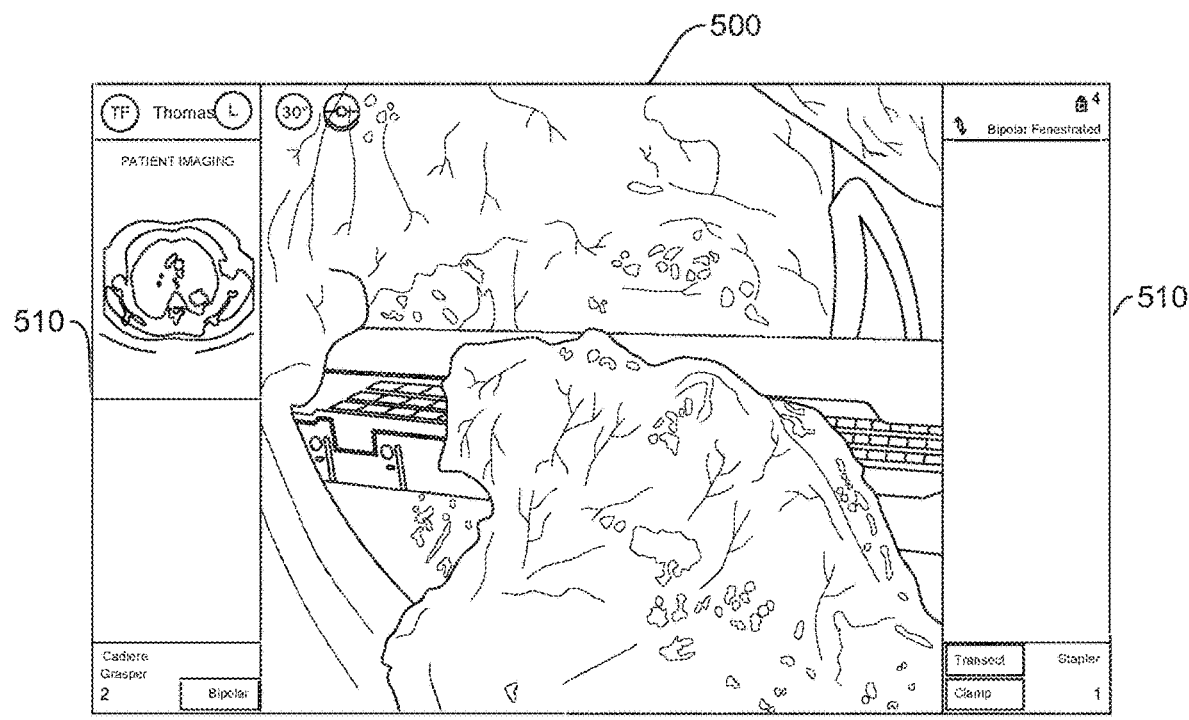
FIG. 27 is an illustration of a GUI of a robotic surgical system of an embodiment in which a CT image is pinned to a display area in a second region.

The various panels of the first and/or second display regions 500, 510 can be dynamically changed. For example, as shown in FIGS. 24 and 25, the display panel in the second region 510 in FIG. 23 that shown a CT image can be moved to the larger first region 510, and the image of the surgical site can be moved to a panel in the second region 510. Each thumbnail may be associated with a single image, or may be associated with an image series (e.g., multiple images taken on the same date). With the large CT image shown, the surgeon can use the user input devices to "flip" through different images in the set of CT scans. If the surgeon finds an image of interest, the surgeon can "pin" that particular image to the second display region 510 (e.g., by squeezing both user input devices). When this occurs, a message is displayed over the CT image in the first display region 500 confirming the pin operation occurred (FIG. 26), and the CT image is later pinned in the second display region 510 (FIG. 27).

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

What is claimed is:

1. A robotic surgical system comprising:
   a robotic surgical instrument;
   one or more handheld user input devices configured for control of a robotic arm connected with the robotic surgical instrument;
   a display device; and
   a processor configured to:
   display, in a first region of the display device, a view of a surgical site inside a patient taken by an image capture device of the robotic surgical system; and
   display, in a second region of the display device, user feedback information about control of the robotic arm in response to the handheld user input devices;
   wherein the processor is further configured to overlay a guidance message on top of the view of the surgical site in the first region, wherein the guidance message provides user instructions for interacting with the one or more handheld user input devices to engage the robotic surgical instrument, and wherein only guidance messages are overlaid on top of the view of the surgical site.

2. The robotic surgical system of claim 1, wherein the guidance message instructs a user to match a grip of the one or more handheld user input devices with a grip of the robotic surgical instrument.

3. The robotic surgical system of claim 2, wherein the guidance message comprises a graphic that changes as the grip of the one or more handheld user input devices changes.

4. The robotic surgical system of claim 1, wherein the guidance message instructs a user to press a foot-operated control.

5. The robotic surgical system of claim 1, wherein the user feedback information displayed in the second region comprises one or more of the following: an error, a warning, an alert, or a notification.

6. The robotic surgical system of claim 1, wherein the user feedback information displayed in the second region comprises one or more of the following: information on an energy level applied by engaging one of the plurality of user input devices, a warning that one of the plurality of user input devices is approaching a workspace limit, a message that one of the plurality of user input devices has exceeded a workspace limit, a message that a rotation limit has been reached, a message that eye contact has been lost, and a message that one of the plurality of user input devices has been dropped.

7. The robotic surgical system of claim 1, wherein the processor is further configured to display an application in the second region.

8. The robotic surgical system of claim 7, wherein the processor is further configured to swap the display of the endoscopic view of the surgical site and the display of the application between the first and second regions.

9. A robotic surgical system comprising:
a display device for displaying a graphical user interface, wherein the graphical user interface comprises a first region displaying a view of a surgical site with a surgical instrument inside a patient taken by an endoscopic camera of the robotic surgical system and a second region; and
a processor configured to cause display of user feedback information about control of a robotic arm or the surgical instrument in response to a user input device in the second region and overlay a guidance message on top of the view of the surgical site in the first region, wherein the guidance message provides user instructions for interacting with the user input device to engage a robotic arm connected with the surgical instrument of the robotic surgical system.

10. The robotic surgical system of claim 9, wherein the guidance message instructs a user to match a grip of the user input device with a grip of the robotic arm.

11. The robotic surgical system of claim 10, wherein the guidance message comprises a graphic that changes as the grip of the user input device changes.

12. The robotic surgical system of claim 9, wherein the user feedback information displayed in the second region comprises one or more of the following: an error, a warning, an alert, or a notification.

13. The robotic surgical system of claim 9, wherein the guidance message instructs a user to press a foot-operated control.

14. The robotic surgical system of claim 9, wherein the user feedback information displayed in the second region comprises one or more of the following: information on an energy level applied by engaging the user input device, a warning that the user input device is approaching a workspace limit, a message that the user input device has exceeded a workspace limit, a message that a rotation limit has been reached, a message that eye contact has been lost, and a message that the user input device has been dropped.

15. The robotic surgical system of claim 9, wherein the processor is further configured to display an application in the second region.

16. The robotic surgical system of claim 15, wherein the processor is further configured to swap the display of the view of the surgical site and the display of the application between the first and second regions.

* * * * *